(12) United States Patent
Kertesz et al.

(10) Patent No.: US 6,552,028 B2
(45) Date of Patent: Apr. 22, 2003

(54) 2,4-SUBSTITUTED PYRROLIDINE DERIVATIVES-CCR-3 RECEPTOR ANTAGONISTS

(75) Inventors: Denis John Kertesz, Mountain View, CA (US); Michael Garret Roepel, San Francisco, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 10/034,034

(22) Filed: Dec. 19, 2001

(65) Prior Publication Data

US 2002/0198255 A1 Dec. 26, 2002

Related U.S. Application Data

(60) Provisional application No. 60/256,585, filed on Dec. 19, 2000.

(51) Int. Cl.$^7$ .................. C07D 403/12; A61K 31/506
(52) U.S. Cl. .................. 514/274; 544/318; 548/571
(58) Field of Search .................. 544/318; 514/274; 548/571

(56) References Cited

U.S. PATENT DOCUMENTS 6,166,015 A  12/2000  Rogers et al.

FOREIGN PATENT DOCUMENTS

| WO | WO 00/31032 | 6/2000 |
|----|-------------|--------|
| WO | WO 00/35449 | 6/2000 |
| WO | WO 00/35451 | 6/2000 |
| WO | WO 00/35452 | 6/2000 |
| WO | WO 00/35453 | 6/2000 |
| WO | WO 00/35454 | 6/2000 |
| WO | WO 00/35876 | 6/2000 |
| WO | WO 00/35877 | 6/2000 |

*Primary Examiner*—Joseph K. McKane
*Assistant Examiner*—Rebecca L Anderson
(74) *Attorney, Agent, or Firm*—Rohan Peries

(57) ABSTRACT

This invention relates to certain 2,4-substituted pyrrolidine derivatives that are CCR-3 receptor antagonists, pharmaceutical compositions containing them, methods for their use and methods for preparing these compounds.

28 Claims, No Drawings

2,4-SUBSTITUTED PYRROLIDINE DERIVATIVES-CCR-3 RECEPTOR ANTAGONISTS

CROSS REFERENCE TO RELATED APPLICATION

This application claims benefit under Title 35 U.S.C. 119 (e) of U.S. Provisional Application No. 60/256,585 filed Dec. 19, 2000.

FIELD OF THE INVENTION

This invention relates to certain 2,4-substituted pyrrolidine derivatives that are CCR-3 receptor antagonists, pharmaceutical compositions containing them, methods for their use and methods for preparing these compounds.

BACKGROUND INFORMATION

Tissue eosinophilia is a feature of a number of pathological conditions such as asthma, rhinitis, eczema and parasitic infections ((see Bousquet, J. et al. *N. Eng. J. Med.* 323: 1033–1039 (1990) and Kay, A. B. and Corrigan, C. J. *Br. Med. Bull.* 48:51–64 (1992)). In asthma, eosinophil accumulation and activation are associated with damage to bronchial epithelium and hyperresponsiveness to constrictor mediators. Chemokines such as RANTES, eotaxin and MCP-3 are known to activate eosinophils ((see Baggiolini, M. and Dahinden, C. A. *Immunol. Today.* 15:127–133 (1994), Rot, A. M. et al. *J. Exp. Med.* 176, 1489–1495 (1992) and Ponath, P. D. et al. *J. Clin. Invest.,* Vol. 97, #3, 604–612 (1996)). However, unlike RANTES and MCP-3 which also induce the migration of other leukocyte cell types, eotaxin is selectively chemotactic for eosinophils ((see Griffith-Johnson, D. A et al. *Biochem. Biophy. Res. Commun.* 197:1167 (1993) and Jose, P. J. et al. *Biochem. Biophy. Res. Commun.* 207, 788 (1994)). Specific eosinophil accumulation was observed at the site of administration of eotaxin whether by intradermal or intraperitoneal injection or aerosol inhalation ((see Griffith-Johnson, D. A et al. *Biochem. Biophy. Res. Commun.* 197:1167 (1993); Jose, P. J. et al. *J. Exp. Med.* 179, 881–887 (1994); Rothenberg, M. E. et al. *J. Exp. Med.* 181, 1211 (1995) and Ponath. P. D. *J. Clin. Invest.,* Vol. 97, #3, 604–612 (1996)).

Glucocorticoids such as dexamethasone, methprednisolone and hydrocortisone have been used for treating many eosinophil-related disorders, including bronchial asthma (R. P. Schleimer et. al., *Am. Rev. Respir. Dis.,* 141, 559 (1990)). The glucocorticoids are believed to inhibit IL-5, IL-3 mediated eosinophil survival in these diseases. However, prolonged use of glucocorticoids can lead to side effects such as glaucoma, osteoporosis and growth retardation in the patients (see Hanania N. A et al., *J. Allergy and Clin. Immunol.,* Vol. 96, 571–579 (1995) and Saha M. T. et al, *Acta Paediatrica,* Vol. 86, #2, 138–142 (1997)). It is therefore desirable to have an alternative means of treating eosinophil related diseases without incurring these undesirable side effects.

Recently, the CCR-3 receptor was identified as a major chemokine receptor that eosinophils use for their response to eotaxin, RANTES and MCP-3. When transfected into a murine pre-β lymphoma line, CCR-3 bound eotaxin, RANTES and MCP-3 and conferred chemotactic responses on these cells to eotaxin, RANTES and MCP-3 (see Ponath. P. D. et al. *J. Exp. Med.* 183, 2437–2448 (1996)). The CCR-3 receptor is expressed on the surface of eosinophils, T-cells (subtype Th-2), basophils and mast cells and is highly selective for eotaxin. Studies have shown that pretreatment of eosinophils with an anti-CCR-3 mAb completely inhibits eosinophil chemotaxis to eotaxin, RANTES and MCP-3 (see Heath H. et al. *J. Clin. Invest., Vol.* 99, #2, 178–184 (1997)). Applicants' co-pending U.S. patent application Ser. Nos. 09/134,013, issued as U.S. Pat. No. 6,323,223 filed Aug. 14, 1998 and WO 00/31032 discloses CCR-3 antagonists that inhibit eosinophilic recruitment by chemokine such as eotaxin. Therefore, blocking the ability of the CCR-3 receptor to bind RANTES, MCP-3 and eotaxin and thereby preventing the recruitment of eosinophils should provide for the treatment of eosinophil-mediated inflammatory diseases.

The present invention concerns novel pyrrolidine derivatives which are capable of inhibiting the binding of eotaxin to the CCR-3 receptor and thereby provide a means of combating eosinophil induced diseases, such as asthma.

SUMMARY OF THE INVENTION

In a first aspect, this invention provides a compound of Formula (I):

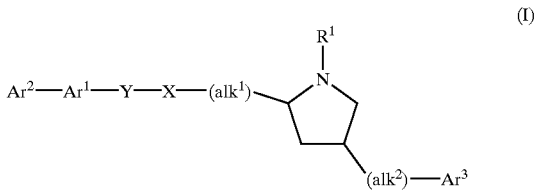

wherein:

$R^1$ is hydrogen, alkyl, acyl, heteroalkyl, —$CONR^3R^4$ (where $R^3$ and $R^4$ are independently hydrogen or alkyl), —$COOR^5$ (where $R^5$ is hydrogen, alkyl or heteroalkyl), or —$SO_2R^6$ where $R^6$ is alkyl;

$alk^1$ is an alkylene chain of 1 to 6 carbon atoms;

X is —NHCO— or —CONH—;

Y is an alkylene chain of 1 to 3 carbon atoms or an alkylene chain of 2 or 3 carbon atoms wherein one of the carbon atoms is replaced by a heteroatom selected from the group consisting of —O—, —$NR^b$— [where $R^b$ is hydrogen, alkyl, acyl, —$CONR^7R^8$ (where $R^7$ and $R^8$ are independently hydrogen or alkyl), —$COOR^9$ (where $R^9$ is hydrogen, alkyl or heteroalkyl), aryl, or aralkyl)] and —S(O)n— wherein n is 0 to 2;

$Ar^1$ is a heteroaryl group or phenyl group wherein the heteroaryl or phenyl group is substituted, in addition to the $Ar^2$ group, with a substituent selected from the group consisting of hydrogen, halo, alkyl, alkoxy, nitro, amido, aminosulfonyl and sulfonylamino;

$Ar^2$ is aryl;

$alk^2$ is an alkylene chain of 1 to 6 carbon atoms wherein one of the carbon atoms is optionally replaced by —CO—, —NRC— [where $R^c$ is hydrogen, alkyl, acyl, —$CONR^{10}R^{11}$ (where $R^{10}$ and $R^{11}$ are independently hydrogen or alkyl), —$COOR^{12}$ (where $R^{12}$ is hydrogen, alkyl or heteroalkyl), aryl, or aralkyl)] or —S(O)n1— wherein n1 is 0 to 2;

$Ar^3$ is cycloalkyl, aryl or heteroaryl; or a pharmaceutically acceptable salts thereof.

In a second aspect, this invention provides a pharmaceutical composition comprising a therapeutically effective amount of a compound of Formula (I) or it's pharmaceutically acceptable salt and a pharmaceutically acceptable excipient.

In a third aspect, this invention provides a method of treatment of a disease in a mammal treatable by administration of a CCR-3 receptor antagonist, comprising administration of a pharmaceutical composition comprising a therapeutically effective amount of a compound of Formula (I) or it's pharmaceutically acceptable salt and a pharmaceutically acceptable excipient. The disease states include respiratory diseases such as asthma.

In a fourth aspect, this invention provides a process for preparing compounds of Formula (I).

In a fifth aspect, this invention provides the use of a compound of Formula (I) or it's pharmaceutically salt in the preparation of medicament for the treatment of a disease mediated by a CCR-3 receptor. The disease states include respiratory diseases such as asthma.

DETAILED DESCRIPTION OF THE INVENTION

Definitions

Unless otherwise stated, the following terms used in the specification and claims have the meanings given below:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, n-butyl, iso-butyl, tert-butyl, n-pentyl, 2-, 3-, methylbutyl, neopentyl, and the like.

"Alkylene" means a linear saturated divalent hydrocarbon radical of one to six carbon atoms or a branched saturated divalent hydrocarbon radical of three to six carbon atoms, e.g., methylene, (2-propyl)methylene, ethylene, methyethylene, (2-propyl)ethylene, propylene, 1- or 2-methylpropylene, 1- or 2-ethylpropylene, pentylene, and the like.

"Acyl" means a radical —C(O)R where R is alkyl, haloalkyl, alkyl substituted with carboxy, alkoxycarbonyl, heterocycle, or aryloxycarbonyl, aryl, aralkyl, heteroaryl, or heteroaralkyl, e.g., acetyl, trifluoroacetyl, —C(O)CH$_2$CO$_2$H, —C(O)—CH$_2$—CO$_2$CH$_3$, benzoyl, thenoyl, and the like.

"Halo" means fluoro, chloro, bromo or iodo, preferably fluoro and chloro.

"Haloalkyl" means alkyl substituted with one or more same or different halo atoms, e.g., —CH$_2$Cl, —CF$_3$, —CH$_2$CF$_3$, —CH$_2$CCl$_3$, and the like.

"Monoalkylamino" means a radical —NHR where R is alkyl, e.g., methylamino, ethylamino, (1-methylethyl)amino, and the like.

"Dialkylamino" means a radical —NRR' where R and R' are independently alkyl. Representative examples include, but are not limited to, dimethylamino, methylethylamino, di(1-methylethyl)amino, and the like.

"Sulfonylamino" means a radical —NHSO$_2$R where R is hydrogen or alkyl. Representative examples include, but are not limited to, —NH$_2$SO$_2$CH$_3$, and the like.

"Aminosulfonyl" means a radical —SO$_2$NHR where R is alkyl. Representative examples include, but are not limited to, —SO$_2$NH$_2$, —SO$_2$NHCH$_3$, and the like.

"Alkylsulfonyl" means a radical —SO$_2$R where R is alkyl. Representative examples include, but are not limited to, methylsulfonyl, ethylsulfonyl, and the like.

"Aryl" means a monovalent monocyclic or bicyclic aromatic hydrocarbon radical of 6 to 10 ring atoms. The aryl ring may be optionally substituted independently with one or more substituents, preferably one, two or three substituents selected from alkyl, haloalkyl, alkylthio, alkoxy, halo, cyano, nitro, amino, hydroxylamino, hydroxy, alkylsulfonyl, sulfonylamino, aminosulfonyl, —NR'R" (where R' is hydrogen or alkyl and R" is hydrogen, alkyl, acyl, alkylsulfonyl) and —COOR (where R is hydrogen or alkyl). More specifically the term aryl includes, but is not limited to, phenyl, 1-naphthyl, 2-naphthyl and derivatives thereof such as 2,3-dichlorophenyl, 3,4-dichlorophenyl, methoxyphenyl, 2,3-dimethoxyphenyl, 3,4-dimethoxyphenyl, and the like.

"Heteroaryl" means a monovalent monocyclic or bicyclic aromatic radical of 5 to 10 ring atoms containing one, two, or three ring heteroatoms selected from N, O, or S, the remaining ring atoms being C. The aromatic radical is optionally fused to a phenyl and optionally substituted with one or two substituents from alkyl, haloalkyl, alkoxy, halo, cyano, nitro, amino, monoalkylamino, dialkylamino, hydroxy and —COOR (where R is hydrogen or alkyl). More specifically the term heteroaryl includes, but is not limited to pyridyl, pyrrolyl, thiophene, pyrazolyl, thiazolyl, imidazolyl, pyrimidinyl, thiadiazolyl, indolyl, carbazolyl, azaindolyl, benzofuranyl, benzimidazolyl, benzthiazolyl, quinoxalinyl, benzotriazolyl, benzisoxazolyl, purinyl, quinolinyl, isoquinolinyl, benzopyranyl, and derivatives thereof.

"Heterocycle" or "Heterocyclyl" means a saturated or unsaturated cyclic radical of 3 to 8 ring atoms in which one or two ring atoms are heteroatoms selected from N, O, or S(O)$_n$ (where n is an integer from 0 to 2), the remaining ring atoms being C, where one or two C atoms may optionally be replaced by a carbonyl group. The heterocyclo ring may be optionally substituted independently with one, two or three substituents selected from alkyl, haloalkyl, aryl, aralkyl, heteroaryl, heteroaralkyl, halo, cyano, amino, monoalkylamino, dialkylamino, —COOR (where R is hydrogen or alkyl), or —XR (where X is O and R is hydrogen or alkyl. Representative examples include, but are not limited to, tetrahydropyranyl, piperidino, piperazino, pyrrolidino, and the like.

"Heteroalkyl" means an alkyl radical as defined above, carrying a substituent containing a heteroatom selected from N, O, S(O)$_n$ where n is an integer from 0 to 2. Representative substituents include —NR$^a$R$^b$, —OR$^a$ or —S(O)$_n$R$^c$, wherein n is an integer from 0 to 2, R$^a$ is hydrogen, alkyl, haloalkyl, or —COR (where R is alkyl, hydroxy, or alkoxy), R$^b$ is hydrogen or alkyl and R$^c$ is hydrogen, alkyl, amino, monoalkylamino, or dialkylamino. Representative examples include, but are not limited to 2-methoxyethyl, hydroxymethyl, methoxymethyl, 2-hydroxyethyl, 3-hydroxypropyl, -aminoethyl, 2-dimethylaminoethyl, and the like.

"Hydroxyalkyl" means a linear monovalent hydrocarbon radical of two to six carbon atoms or a branched monovalent hydrocarbon radical of three or six carbons substituted with one or two hydroxy groups, provided that if two hydroxy groups are present they are not both on the same carbon atom. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl. Hydroxyalkyl is a subset of heteroalkyl group.

"Aralkyl" means a radical —R$^a$R$^b$ where R$^a$ is an alkylene group and R$^b$ is an aryl group as defined above e.g., benzyl, phenylethyl, 3-(3-chlorophenyl)-2-methylpentyl, and the like.

"Alkoxy" means a radical —OR where R is an alkyl, respectively as defined above e.g., methoxy, ethoxy, propoxy, and the like.

"Optional" or "optionally" means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

"Amino-protecting group" refers to those organic groups intended to protect nitrogen atoms against undesirable reactions during synthetic procedures e.g., benzyl, benzyloxycarbonyl (CBZ), t-butoxycarbonyl (BOC), trifluoroacetyl, and the like.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. For example, if the $R^1$ substituent in a compound of Formula (I) is alkyl, then the carbon to which it is attached is an asymmetric center and the compound of Formula (I) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. "A pharmaceutically acceptable excipient" as used in the specification and claims includes both one and more than one such excipient.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Leaving group" has the meaning conventionally associated with it in synthetic organic chemistry i.e., an atom or group capable of being displaced by a nucleophile and includes halogen, alkanesulfonyloxy, arenesulfonyloxy, ester, or amino such as chloro, bromo, iodo, mesyloxy, tosyloxy, trifluorosulfonyloxy, methoxy, N,O-dimethylhydroxylamino, and the like.

"Pro-drugs" means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, sulfhydryl or amino group in compound (I) is bonded to any group that may be cleaved in vivo to regenerate the free hydroxyl, amino, or sulfhydryl group, respectively. Unless indicated otherwise, the description of a particular compound in the specification and claims is intended to include the prodrugs of a compound of Formula (I). Examples of prodrugs include, but are not limited to esters (e.g., acetate, formate, and benzoate derivatives), carbamates (e.g., N,N-dimethylaminocarbonyl) of hydroxy functional groups in compounds of Formula (I), and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Nomenclature

The nomenclature used in this application is generally based on the IUPAC recommendations.

The pyrrolidine ring is numbered as follows:

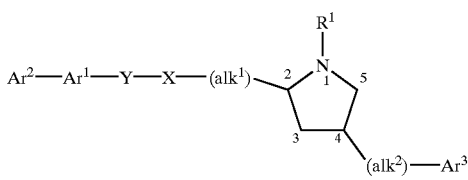

and the compounds of the invention are named as:

A compound of Formula (I) where $Ar^3$ is 3,4-dichlorophenyl, $alk^2$ is —$CH_2$—, $R^1$ is hydrogen, $alk^1$ is —$(CH_2)_2$—, X is —CONH—, Y is —$(CH_2)_2$— and $Ar^1$ is pyrimidin-2-yl, $Ar^2$ is 4-methoxyphenyl and is at the 5-position of the pyrimidine ring, is named N-[4-(3,4-dichlorobenzyl)pyrrolidin-2-ylethyl]-3-[5-(4-methoxyphenyl)pyrimidin-2-yl]propionamide.

A compound of Formula (I) where $Ar^3$ is 3,4-dichlorophenyl, $alk^2$ is —$CH_2$—, $R^1$ is methyl, $alk^1$ is —$(CH_2)_2$—, X is —CONH—, Y is —$SCH_2$— and $Ar^1$ is pyrimidin-2-yl, $Ar^2$ is 3,4-methoxyphenyl and is at the 5-position of the pyrimidine ring, is named is named N-[4-(3,4-dichlorobenzyl)-1-methylpyrrolidin-2-ylethyl]-2-[5-(3,4-dimethoxyphenyl)pyrimidin-2-ylsulfanyl]acetamide.

A compound of Formula (I) where $Ar^3$ is 3,4-dichlorophenyl, $alk^2$ is —$CH_2$—, $R^1$ is methyl, $alk^1$ is —$(CH_2)_2$—, X is —CONH—, Y is —$OCH_2$— and $Ar^1$ is pyrimidin-2-yl, $Ar^2$ is 3,4-methoxyphenyl and is at the 5-position of the pyrimidine ring, is named is named N-[4-(3,4-dichlorobenzyl)-1-methylpyrrolidin-2-ylethyl]-2-[5-(3,4-dimethoxyphenyl)pyrimidin-2-yloxy]acetamide.

A compound of Formula (I) where $Ar^3$ is 3,4-dichlorophenyl, $alk^2$ is —$CH_2$—, $R^1$ is methyl, $alk^1$ is —$(CH_2)_2$—, X is —CONH—, Y is —$NHCH_2$— and $Ar^1$ is pyrimidin-2-yl, $Ar^2$ is 3,4-methoxyphenyl and is at the 5-position of the pyrimidine ring, is named is named N-[4-(3,4-dichlorobenzyl)-1-methylpyrrolidin-2-ylethyl]-2-[5-(3,4-dimethoxyphenyl)pyrimidin-2-ylamino]acetamide.

A compound of Formula (I) where $Ar^3$ is 3,4-dichlorophenyl, $alk^2$ is —$CH_2$—, $R^1$ is acetyl, $alk^1$ is —$(CH_2)_2$—, X is —CONH—, Y is —$SCH_2$— and $Ar^1$ is pyrimidin-2-yl, $Ar^2$ is 3,4-methoxyphenyl and is at the 5-position of the pyrimidine ring, is named is named N-[1-acetyl-4-(3,4-dichlorobenzyl)pyrrolidin-2-ylethyl]-2-[5-(3,4-dimethoxyphenyl)pyrimidin-2-ylsulfanyl]-acetamide.

A compound of Formula (I) where $Ar^3$ is 3,4-dichlorophenyl, $alk^2$ is —$CH_2$—, $R^1$ is hydrogen, $alk^1$ is —$(CH_2)$—, X is —CONH—, Y is —$CH_2NH$—, $Ar^1$ is pyrimidinyl, and Ar is 4-methoxyphenyl and is at the 5-position of the pyrimidine ring, is named 1-[4-(3,4-dichlorobenzyl)pyrrolidin-2-ylmethyl]-3-(4-methoxyphenylpyrimidin-2-ylmethyl)urea.

Representative Compounds of this Invention are as Follows:

1. Representative compounds of Formula (I):

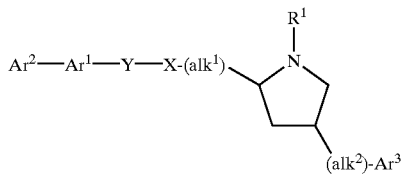

| CPD # | Stereo-chem | $Ar^2$—$Ar^1$ | Y | X | $alk^1$ | $R^1$ | $alk^2$ | $Ar^3$ |
|---|---|---|---|---|---|---|---|---|
| 1. | 2S,4R | 5-(3,4-dimethoxyphenyl)-pyrimidin-2-yl | —$SCH_2$— | —CONH— | —$(CH_2)_2$— | —$COCH_2CO_2H$ | —$CH_2$— | 3,4-dichlorophenyl |
| 2. | 2S,4R | 5-(3,4-dimethoxyphenyl)-pyrimidin-2-yl | —$SCH_2$— | —CONH— | —$(CH_2)_2$— | —$COCH_2CO_2CH_3$ | —$CH_2$— | 3,4-dichlorophenyl |
| 3. | 2S,4R | 5-(3,4-dimethoxyphenyl)-pyrimidin-2-yl | —$SCH_2$— | —CONH— | —$(CH_2)_2$— | —$SO_2CH_3$ | —$CH_2$— | 3,4-dichlorophenyl |
| 4. | 2S,4R | 5-(3,4-dimethoxyphenyl)-pyrimidin-2-yl | —$SCH_2$— | —CONH— | —$(CH_2)_2$— | —$COCH_3$ | —$CH_2$— | 3,4-dichlorophenyl |
| 5. | 2R,4S | 5-(3,4-dimethoxyphenyl)-pyrimidin-2-yl | —$SCH_2$— | —CONH— | —$(CH_2)_2$— | hydrogen | —$CH_2$— | 3,4-dichlorophenyl |
| 6. | 2S,4R | 5-(3,4-dimethoxyphenyl)-pyrimidin-2-yl | —$SCH_2$— | —CONH— | —$(CH_2)_2$— | —$COOC(CH_3)_3$ | —$CH_2$— | 3,4-dichlorophenyl |
| 7. | 2S,4R | 5-(3,4-dimethoxyphenyl)-pyrimidin-2-yl | —$SCH_2$— | —CONH— | —$(CH_2)_2$— | hydrogen | —$CH_2$— | 3,4-dichlorophenyl |
| 8. | 2S,4R | 5-(phenyl)pyrimidin-2-yl | —$SCH_2$— | —CONH— | —$(CH_2)_2$— | hydrogen | —$CH_2$— | 3,4-dichlorophenyl |
| 9. | 2R,4S | 5-(phenyl)-pyrimidin-2-yl | —$SCH_2$— | —CONH— | —$(CH_2)_2$— | hydrogen | —$CH_2$— | 3,4-dichlorophenyl |
| 10. | 2R,4R | 5-(phenyl)pyrimidin-2-yl | —$SCH_2$— | —CONH— | —$(CH_2)$— | methyl | —$CH_2$— | 3,4-dichlorophenyl |
| 11. | 2S,4S | 5-(phenyl)-pyrimidin-2-yl | —$SCH_2$— | —CONH— | —$(CH_2)$— | methyl | —$CH_2$— | 3,4-dichlorophenyl |
| 12. | 2S,4R | 5-(phenyl)pyrimidin-2-yl | —$SCH_2$— | —CONH— | —$(CH_2)$— | methyl | —$CH_2$— | 3,4-dichlorophenyl |
| 13. | 2S,4R | 5-(phenyl)pyrimidin-2-yl | —$SCH_2$— | —CONH— | —$(CH_2)_2$ — | methyl | —$CH_2$— | 3,4-dichlorophenyl |
| 14. | 2R,4S | 5-(phenyl)pyrimidin-2-yl | —$SCH_2$— | —CONH— | —$(CH_2)$— | methyl | —$CH_2$— | 3,4-dichlorophenyl |
| 15. | 2S,4R | 5-(3,4-dimethoxyphenyl)-pyrimidin-2-yl | —$(CH_2)_2$— | —CONH— | —$(CH_2)_2$— | hydrogen | —$CH_2$— | 3,4-dichlorophenyl |

Preferred Embodiments

While the broadest definition of this invention is set forth in the Summary of the Invention, certain compounds of Formula (I) are preferred.

(A) A preferred group of compounds of Formula (I) is represented by Formula (Ia):

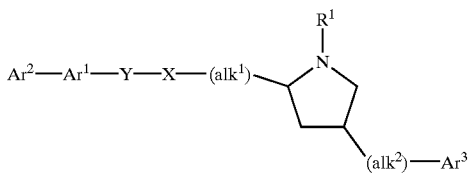

(Ia)

wherein:
R¹ is hydrogen, alkyl, acyl, heteroalkyl, —CONR³R⁴ (where R³ and R⁴ are independently hydrogen or alkyl), —COOR⁵ (where R⁵ is hydrogen, alkyl or heteroalkyl), or —SO₂R⁶ where R⁶ is alkyl;
alk² is an alkylene chain of 1 to 6 carbon atoms;
X is —NHCO— or —CONH—;
Y is —O—(CH₂)—, —O—(CH₂)₂—, —O—(CHCH₃)—, —NR^b—(CH₂)—, —NR^b—(CH₂)₂—, —NR^b—(CHCH₃)— [where R^b is hydrogen, alkyl, acyl, —CONR⁷R⁸ (where R⁷ and R⁸ are independently hydrogen or alkyl), —COOR⁹ (where R⁹ is hydrogen, alkyl or heteroalkyl), aryl, or aralkyl)], —S(O)n—(CH₂)—, —S(O)n—(CH₂)₂—, or —S(O)n—(CHCH₃)— where n is 0 to 2;
Ar¹ is a heteroaryl group or phenyl group wherein the heteroaryl or phenyl group is substituted, in addition to the Ar² group, with a substituent selected from the group consisting of hydrogen, halo, alkyl, alkoxy, nitro, amido, aminosulfonyl and sulfonylamino;
Ar² is aryl;
alk² is an alkylene chain of 1 to 6 carbon atoms wherein one of the carbon atoms is optionally replaced by —CO—, —NR^c— [where R^c is hydrogen, alkyl, acyl, —CONR¹⁰R¹¹ (where R¹⁰ and R¹¹ are independently hydrogen or alkyl), —COOR₁₂ (where R¹² is hydrogen, alkyl or heteroalkyl), aryl, or aralkyl)] or —S(O)n1— wherein n1 is 0 to 2;
Ar³ is cycloalkyl, aryl or heteroaryl; or a pharmaceutically acceptable salts thereof.
Preferably, R¹ is hydrogen, alkyl, acyl, or —SO₂R^a where R^a is alkyl. More preferably, R¹ is hydrogen, methyl, ethyl, acetyl, trifluoroacetyl, —COCH₂CO₂H, —COCH₂CO₂R' where R' is alkyl, or —SO₂CH₃. Even more preferably, R¹ is hydrogen, methyl, acetyl, —COCH₂CO₂H, —COCH₂CO₂CH₃, —CO₂-tert-butyl.
Preferably, alk¹ is an alkylene chain of 1 to 3 carbon atoms; more preferably methyl, ethyl or n-propyl, even more preferably methyl or ethyl.
Preferably, X is —CONH—.
Preferably, Y is —SCH₂—, —OCH₂— or —NHCH₂—. More preferably, Y is —SCH₂— or —OCH₂—.
Preferably, Ar¹ is a heteroaryl group. More preferably Ar¹ is pyridyl or pyrimidinyl. More preferably Ar¹ is pyridin-2-yl or pyrimidin-2-yl. Even more preferably pyrimidin-2-yl.
Preferably, Ar² is aryl optionally substituted with one or two substituents selected from the group consisting of alkoxy, hydroxy, or halo. More preferably, Ar² is phenyl or 3,4-dimethoxyphenyl and is at the 5-position of the pyrimidin-2-yl or pyridin-2-yl ring.
Preferably, alk² is an alkylene group of 1 to 3 carbon atoms, more preferably —CH₂—.
Preferably, Ar³ is aryl. More preferably, Ar³ is phenyl optionally substituted with 1 or 2 halo groups. Even more preferably, Ar³ is 3,4-dichlorophenyl.
Preferably, X is —CONH— and Y is —SCH₂— or —OCH₂—.
Preferably, X is —CONH—, Y is —SCH₂— or —OCH₂— and Ar¹ is pyridyl or pyrimidinyl. More preferably Ar¹ is pyridin-2-yl or pyrimidin-2-yl. Even more preferably pyrimidin-2-yl.

(B) Another preferred compounds of Formula (I) are represented by Formula (Ib):

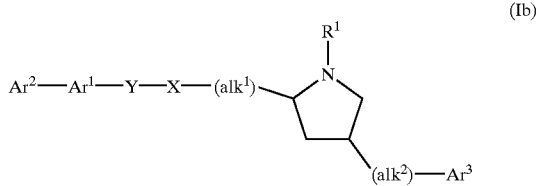

(Ib)

wherein:
R¹ is hydrogen, alkyl, acyl, heteroalkyl, —CONR³R⁴ (where R³ and R⁴ are independently hydrogen or alkyl), —COOR⁵ (where R⁵ is hydrogen, alkyl or heteroalkyl), or —SO₂R⁶ where R⁶ is alkyl;
alk¹ is an alkylene chain of 1 to 6 carbon atoms;
X is —NHCO— or —CONH—;
Y is:
(i) —(CH₂)—, —(CH₂)₂—, —(CH₂)₃—, —(CHCH₃)—, —(CHCH₃)—(CH₂)—, or —(CH₂)—(CHCH₃)—;
(ii) —(CH₂)—O—, —(CH₂)₂—O—, —(CHCH₃)—O—, —(CH₂)—NR^b—, —(CH₂)₂—NR^b—, or —(CHCH₃)—NR^b— [where R^b is hydrogen, alkyl, acyl, —CONR⁷R⁸ (where R⁷ and R⁸ are independently hydrogen or alkyl), —COOR⁹ (where R⁹ is hydrogen, alkyl or heteroalkyl), aryl, or aralkyl)] when X is —CONH—;
Ar¹ is a heteroaryl group or phenyl group wherein the heteroaryl or phenyl group is substituted, in addition to the Ar² group, with a substituent selected from the group consisting of hydrogen, halo, alkyl, alkoxy, nitro, amido, aminosulfonyl and sulfonylamino;
Ar² is aryl;
alk² is an alkylene chain of 1 to 6 carbon atoms wherein one of the carbon atoms is optionally replaced by —CO—, —NR^c—[where R^c is hydrogen, alkyl, acyl, —CONR¹⁰R¹¹ (where R¹⁰ and R¹¹ are independently hydrogen or alkyl), —COOR¹² (where R¹² is hydrogen, alkyl or heteroalkyl), aryl, or aralkyl)] or —S(O)n1— wherein n1 is 0 to 2;
Ar³ is cycloalkyl, aryl or heteroaryl; or a pharmaceutically acceptable salts thereof.
Preferably, R¹ is hydrogen, alkyl, acyl, or —SO₂R^a where R^a is alkyl. More preferably, R¹ is hydrogen, methyl, ethyl, acetyl, trifluoroacetyl, —COCH₂CO₂H, —COCH₂CO₂R' where R' is alkyl or —SO₂CH₃. Even more preferably, R¹ is hydrogen, methyl, acetyl, —COCH₂CO₂H, —COCH₂CO₂CH₃, —CO₂-tert-butyl.
Preferably, alk¹ is an alkylene chain of 1 to 3 carbon atoms; more preferably methyl, ethyl or n-propyl, even more preferably methyl or ethyl.
Preferably, X is —CONH—.
Preferably, Y is —CH₂— or —(CH₂)₂—.
Preferably, Y is —(CH₂)—NR^b— or —(CH₂)₂—NR^b— [where R^b is hydrogen, alkyl, acyl, —CONR⁷R⁸ (where R⁷ and R⁸ are independently hydrogen or alkyl), —COOR⁹ (where R⁹ is hydrogen, alkyl or heteroalkyl), aryl, or aralkyl)] when X is —CONH—;
Preferably, Ar¹ is a heteroaryl group. More preferably pyridyl or pyrimidinyl. More preferably Ar¹ is pyridin-2-yl or pyrimidin-2-yl. Even more preferably pyrimidin-2-yl.
Preferably, Ar² is aryl optionally substituted with one or two substituents selected from the group consisting of alkoxy, hydroxy, or halo. More preferably, Ar² is phenyl or 3,4-dimethoxyphenyl and is at the 5-position of the pyrimidin-2-yl or pyridin-2-yl ring.
Preferably, alk² is an alkylene group of 1 to 3 carbon atoms, more preferably or —CH₂— or —(CH₂)₂—.

Preferably, $Ar^3$ is aryl. More preferably, $Ar^3$ is phenyl optionally substituted with 1 or 2 halo groups. Even more preferably, $Ar^3$ is 3,4-dichlorophenyl.

Preferably, X is —CONH— and Y is —$(CH_2)_2$—.

Preferably, X is —CONH— and Y is —$(CH_2)_2$—NH— or —$CH_2$—NH—.

Preferably, X is —CONH—, Y is —$(CH_2)_2$— and $Ar^1$ is pyridyl or pyrimidinyl. More preferably $Ar^1$ is pyridin-2-yl or pyrimidin-2-yl. Even more preferably pyrimidin-2-yl.

General Synthetic Scheme

The compounds of the present invention can be prepared in a number of ways known to one skilled in the art. Preferred methods include, but are not limited to, the general synthetic procedures described below.

The starting materials and reagents used in preparing these compounds are either available from commercial suppliers such as Aldrich Chemical Co., (Milwaukee, Wis., U.S.A.), Bachem (Torrance, Calif., U.S.A.), Emka-Chemie, or Sigma (St. Louis, Mo., U.S.A.), Maybridge (Dist: Ryan Scientific, P.O. Box 6496, Columbia, S.C. 92960), Bionet Research Ltd., (Cornwall PL32 9QZ, UK), Menai Organics Ltd., (Gwynedd, N. Wales, UK), Butt Park Ltd., (Dist. Interchim, Montlucon Cedex, France) or are prepared by methods known to those skilled in the art following procedures set forth in references such as *Fieser and Fieser's Reagents for Organic Synthesis,* Volumes 1–17 (John Wiley and Sons, 1991); *Rodd's Chemistry of Carbon Compounds,* Volumes 1–5 and Supplementals (Elsevier Science Publishers, 1989), *Organic Reactions,* Volumes 1–40 (John Wiley and Sons, 1991), *March's Advanced Organic Chemistry,* (John Wiley and Sons, 1992), and *Larock's* Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Compounds of Formula (I) where X is —CONH—, $alk^1$ is —$CH_2$—, the other groups are as defined in the Summary of the Invention and the stereochemistry at C2 and C4 carbon atoms of the pyrrolidine ring is (2S,4R) can be prepared as illustrated in described in Scheme I below.

Scheme I

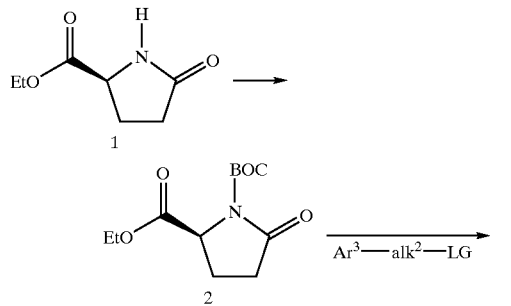

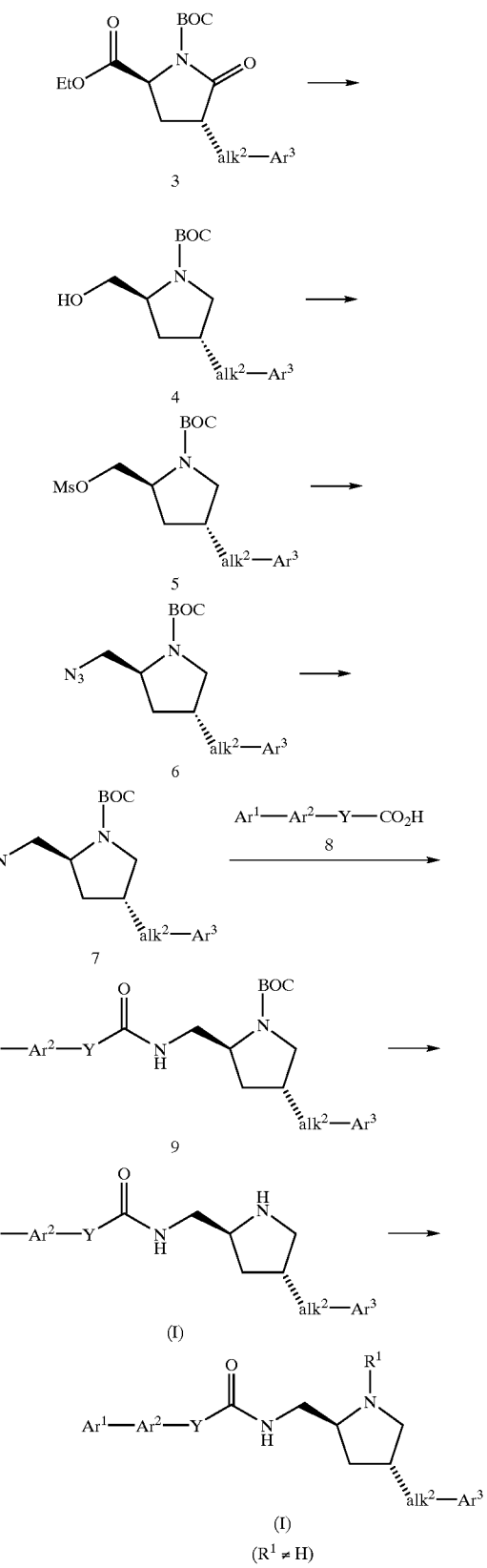

Treatment of ethyl (S)-2-pyrrolidone-5-carboxylate 1 with di-tert-butyldicarbonate provides ethyl (S)-1-tert-butoxycarbonyl-2-pyrrolidone-5-carboxylate 2. The reaction is carried out in an inert organic solvent such as methylene chloride, chloroform, ether and the like, in the presence of an organic amine such as triethylamine and dimethylaminopyridine at room temperature. It will be recognized by a person skilled in the art that other suitable nitrogen protecting groups such a benzyloxycarbonyl can be used.

Treatment of 2 with an aralkyl halide/heteroaralkyl halide of formula $Ar^3$-$alk^2$-LG where $Ar^3$ and $alk^2$ are as defined in the Summary of the Invention and LG is suitable leaving group such as halo, tosylate, mesylate, triflate, and the like, provides a 4-substituted ethyl (S)-1-tert-butoxycarbonyl-2-pyrrolidone-5-carboxylate 3. The reaction is carried out in the presence of a strong base such as LiHDMS, in an ethereal solution such as tetrahydrofuran, diethyl ether and the like. The reaction is initially carried out at approximately −78° C. and then warmed to ambient temperature. Aralkyl halide/heteroaralkyl halide of formula $Ar^3$-$alk^2$-LG are commercially available or they can be prepared by methods skilled in the art. For example, benzyl chloride, 3,4-dichlorobenzyl bromide, and 3-chlorobenzyl chloride are commercially available. Others can be prepared from commercially available alcohols such as benzylalcohol, 2-phenylethanol, 3-phenylpropanol by treating them with a halogenating agent such as $PBr_3$ $POCl_3$ and the like. Alternatively, the alcohols can be converted to mesyl, tosyl, or triflate derivatives by methods well known in the art and can be used in the above reaction in lieu of the alkyl halides.

Reduction of the ester and the amido groups in compound 3 with a suitable reducing agent such as borane in ethereal solution such as tetrahydrofuran at around 40° C. provides the corresponding (2S,4R)-4-(aralkyl or heteroaralkyl)-2-hydroxymethyl-1-tert-butoxycarbonylpyrrolidine of formula 4. The hydroxy group in 4 is converted to a suitable leaving group such as mesylate, tosylate, and the like, by methods well known in the art. The reaction is carried out by treating 4 with methanesulfonyl chloride or p-toluenesulfonyl chloride respectively, in the presence of a base such as triethylamine, pyridine, and the like, and in an inert solvent such as methylene chloride, and the like.

Displacement of the mesylate/tosylate group in compound 5 with an azide ion, followed by reduction of the azido group in the resulting (2S,4R)-4-(aralkyl or heteroaralkyl)-2-azidomethyl-1-tert-butoxycarbonylpyrrolidine of formula 6 then provides a (2S,4R)-4-(aralkyl or heteroaralkyl)-2-aminomethyl-1-tert-butoxycarbonylpyrrolidine of formula 7. The displacement of the mesylate group occurs upon heating 5 with sodium azide in a polar organic solvent such as dimethylformamide.

Reduction of the azido group in 6 to the amino group is carried out under catalytic hydrogenation reaction conditions utilizing a suitable catalyst such as platinum oxide. The reaction is carried out in ethyl acetate at atmospheric pressure and ambient temperature.

Compound 7 is then converted to a compound of Formula (I) where X is —CONH— group by treating 7 with an acid of formula 8 where $Ar^1$, $Ar^2$, and Y are as defined in the Summary of the Invention. The reaction is carried out in the presence of a coupling agent such as 1-(3-dimethylaminopropyl)-3-ethylcarbodiimide, diethylazacarbodimide (DEAD), and the like, and optionally in the presence of a catalyst such as 1-hydroxybenzotriazole hydrate. The reaction is carried out in solvents such as methylene chloride, tetrahydrofuran, and the like and at ambient temperature. Alternatively, the coupling reaction can be carried out by converting 8 to an acid halide such as acid chloride followed by reaction with 7 in the presence of a base such as triethylamine, pyridine, and the like.

Acids of formula 8 are commercially available or they can be prepared by methods well known in the art. For example, 2-(5-methyl-2-phenyloxazol-4-yl)acetic acid, 2-(3-methyl-2-N-phenylpyrazol-4-yl)acetic acid, 2-(2-pyrazin-2-ylthiazol-4-yl)acetic acid, 2-[2-(pyridin-2-yl)-6-trifluoromethylpyrimidin-4-ylsulfanyl]acetic acid, 2-[6-(4-chlorophenyl)pyrimidin-2-ylsulfanyl]acetic acid, 2-(3-phenylpyrazol-1-yl)acetic acid, and 2-methyl-2-(4-thiophenoylphenyl)-acetic acid are commercially available.

Others can be prepared by methods well known in the art. For example, 3-[4-(4-methoxyphenyl)pyrimidin-2-yl]propanoic acid can be prepared by adding a solution of sodium ethoxide (21% wt/vol in ethanol, 10 mL, 30 mmol, 3 equiv.) to a suspension of 2-(4-methoxyphenyl) trimethinium perchlorate (3.3 g, 9.8 mmol) [see, Jutz, C.; Kirchlechner, R.; Seidel, H. Chem. Ber. 102, 2301, (1969)] and 4-amidinobutanoic acid mono HCl (1.5 g, 9.8 mmol) [see, McElvain, S. M.; Schroeder, J. P. J. Am. Chem. Soc., 71, 40, (1949)] in absolute ethanol (40 mL) and heating the reaction mixture at reflux for 12 h. The suspension is concentrated, diluted with water, and washed with ether. The aqueous phase is then made acidic with citric acid (10 g). The precipitates are filtered, washed with water and ether, and dried under high vacuum to yield 3-[4-(4-methoxyphenyl)-pyrimidin-2-yl]propanoic acid.

3-[5-(4-nitrophenyl)pyrimidin-2-yl]-propanoic acid is prepared as follows: Phosphorus oxychloride (83 mL, 0.79 mol) is added slowly to cold, dry dimethylformamide (100 mL) under $N_2$ at such a rate that the temperature does not rise above 5° C. After addition is complete, 4-nitrophenylacetic acid (48 g, 0.26 mol) is added in one portion and the reaction mixture is heated to 85° C. over 1 h. The reaction mixture is cooled, then poured over ice. Solid sodium perchlorate monohydrate (37 g, 0.26 mol) is added to initiate precipitation of the product as the perchlorate salt. Filtration of the solid, followed by washings with cold water, methanol and ether, provides 2-(4-nitrophenyl)trimethinium perchlorate.

A solution of sodium ethoxide (21% wt/vol, in ethanol, 60 mL, 180 mmol, 3 equiv.) is added in one portion to a suspension of 2-(4-nitrophenyl)trimethinium perchlorate (20.8 g, 60 mmol) and 4-amidinopropionic acid mono hydrochloride salt (9.1 g, 60 mmol) in ethanol (300 mL). The suspension is heated at room temperature overnight. The resulting suspension is filtered, washed with ethanol, cold HCl, water and ether, then dried under high vacuum to give 3-[5-(4-nitrophenyl)pyrimidin-2-yl]-propanoic acid which can be hydrogenated under standard catalytic hydrogenation conditions (i.e., using Pd/C catalytst in methanol solvent at atmospheric pressure) to provide 3-{5-(4-aminophenyl)pyrimidin-2-yl]propionic acid.

2-[5-(4-Methoxyphenyl)pyrimidin-2-ylamino]-acetic acid (150 mg) is prepared by adding ethanolic solution of sodium ethoxide (2.7 M, 3.8 mL, 10 mmol, 2.9 equiv.) to a suspension of 2-(4-methoxyphenyl)trimethinium perchlorate salt (1.1 g, 3.4 mmol) and guanidineacetic acid (0.48 g, 4.0 mmol, 1.2 equiv.) in dehydrated ethanol (20 mL). The reaction mixture is stirred at room temperature for 30 min., then at reflux temperature for 3 h. After cooling, the sodium salt is filtered, and the cake is dissolved in 20 mL of water then acidified with 1 M hydrochloric acid. The aqueous layer is extracted with ethyl acetate and the combined organic phases are washed with brine, and dried over sodium sulfate. Removal of the solvent under vacuum affords a solid which contained ~1:1 mixture of regioisomers. The two components are separated using reversed-phase chromatography to give 2-[5-(4-methoxyphenyl)pyrimidin-2-ylamino]acetic acid and the regioisomer.

2-(5-Phenylpyrimidin-2-yloxy)acetic acid and derivatives thereof can be prepared by reacting 5-bromo-2-chloropyrimidine (prepared as described in PCT application Publication No WO 00/31032 the disclosure of which is incorporated herein in it's entirety) with methyl glycolate to give methyl 5-bromopyrimidin-2-yloxyacetate. Coupling of methyl 5-bromopyrimidin-2-yloxyacetate with phenylboronic acid under the reaction conditions described Example 8, step 5 of WO 00/31032, followed by basic hydrolysis of the ester group provides 2-(5-phenylpyrimidin-2-yloxy) acetic acid.

Deprotection of the BOC group then provides a compound of Formula (I) where $R^1$ is hydrogen. The deprotection is carried out under acidic hydrolysis reaction conditions. Suitable acids are trifluoroacetic acid, hydrochloric acid, and the like.

A compound of Formula (I) where $R^1$ is hydrogen can then be converted to other compounds of Formula (I) where $R^1$ is other than hydrogen by methods well known in the art.

A compound of Formula (I) where $R^1$ is hydrogen can be treated with an acyl halide or sulfonyl halide in the presence of a non-nucleophilic base such as triethylamine, pyridine, and the like and in a suitable organic solvent such as methylene chloride, tetrahydrofuran, and the like to provide a corresponding compound of Formula (I) where $R^1$ is acyl. Acyl halides such as acetyl chloride, propionyl chloride, trifluoroacetyl chloride, and monomethoxy malonyl chloride, are commercially available. Sulfonyl halides such as methanesulfonyl chloride are commercially available.

A compound of Formula (I) having an alkoxy substituent for example on the $Ar^1$ or $Ar^3$ group can be converted to a corresponding compound of Formula (I) with a hydroxy group by dealkylation of the alkoxy group under conditions well known in the art. Similarly, a compound of Formula (I) having a nitro substituent for example on the $Ar^1$ or $Ar^3$ group can be converted to a corresponding compound of Formula (I) with an amino group under standard catalytic hydrogenation reaction conditions.

Additionally, utilizing ethyl (R)-2-pyrrolidone-5-carboxylate as the starting material in place of ethyl (S)-2-pyrrolidone-5-carboxylate 1, provides compounds of Formula (I) having (2R,4S) stereochemistry at the pyrrolidine ring.

Compounds of Formula (I) where X is —CONH—, $alk^1$ is —$(CH_2)_2$—, the other groups are as defined in the Summary of the Invention and the stereochemistry at the C2 and C4 carbon atoms of the pyrrolidine ring is (2S,4R) can be prepared as illustrated and described in Scheme II below.

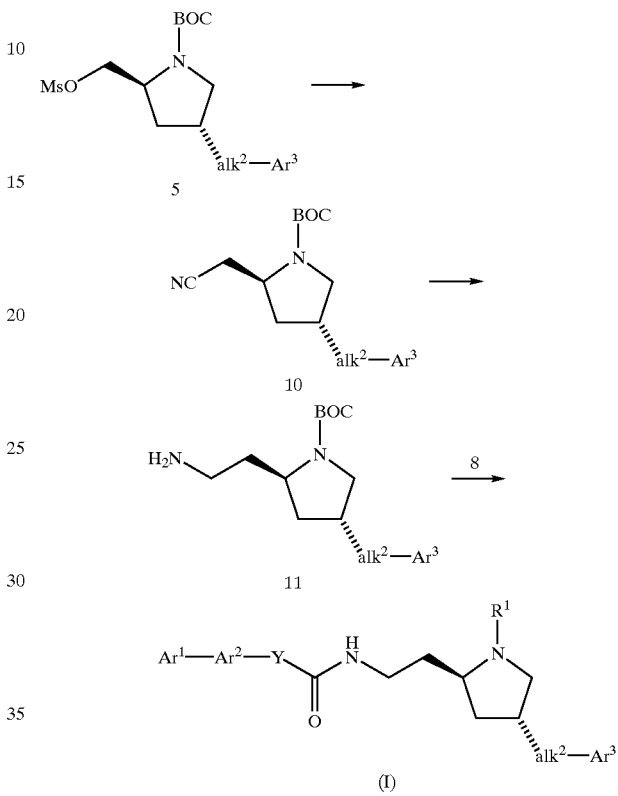

Scheme II

A compound of Formula (I) where X is —CONH— and $alk^1$ is —$(CH_2)_2$— and the other groups are as defined in the Summary of the Invention can be prepared from a compound of formula 5 by first converting it to a cyano derivative of formula 10 by reacting it with sodium or potassium cyanide in dimethyl sulfoxide between 70–90° C. Reduction of the cyano group with a suitable reducing agent such as diborane in tetrahydrofuran then provides aminoethyl derivative of formula 11. Compound 11 is then converted to a compound of Formula (I) where X is —CONH— as described in Scheme I above. Here too, substituting ethyl (R)-2-pyrrolidone-5-carboxylate as the starting material in place of ethyl (S)-2-pyrrolidone-5-carboxylate provides a compound of Formula (I) having (2R, 4S) stereochemistry at the pyrrolidine ring.

Compounds of Formula (I) where X is —CONH—, $R^1$ is alkyl, $alk^1$ is —$(CH_2)$—, the other groups are as defined in the Summary of the Invention and the stereochemistry at C2 and C4 carbon atoms in the pyrrolidine ring is either (2S,4S) or (2S,4R) can be are prepared as illustrated and described in Scheme III below.

Scheme III

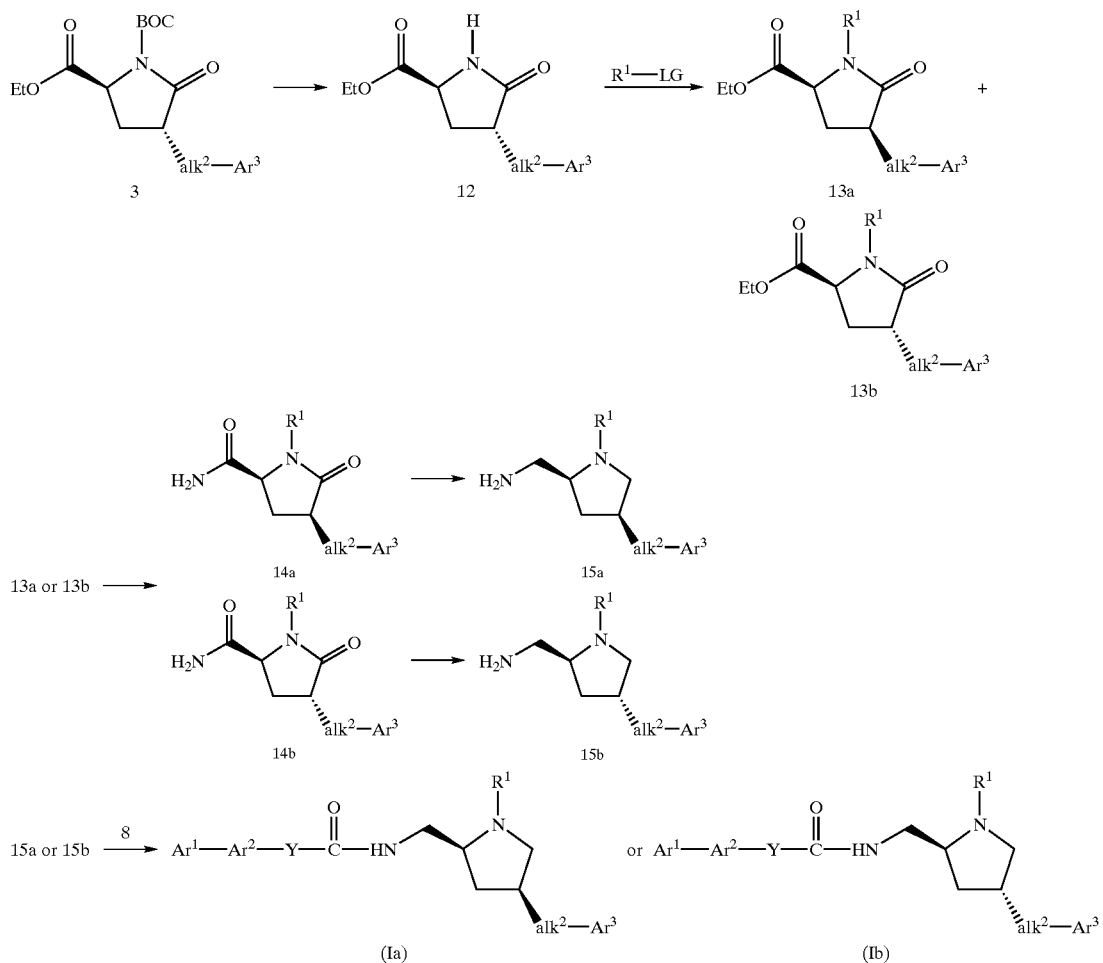

Removal of the tert-butoxycarbonyl group in compound 3 in the presence of a strong base such as sodium hydride above provides a compound of formula 12. Alkylation of 12 with an alkyl halide of formula $R^1LG$ where LG is chloro, bromo or iodo provides a mixture of diastereomers of formula 13a and 13b. The diastereomers can be separated, if desired, by column chromatography as described in Example 4 below. Treatment of 13a or 13b with ammonia in methanol at room temperature provides the corresponding 2-amido-5-oxopyrrolidine derivative of formula 14a or 14b respectively.

Reduction of the 2-amido group in 14a or 14b provides the corresponding 2-aminomethylpyrrolidine derivative of formula 15a or 15b respectively which is then converted to a compound of Formula (I) as described in detail in Scheme I above. The reduction of the amido group is carried out by heating 14a or 14b with diborane in tetrahydrofuran.

Substituting ethyl (R)-2-pyrrolidone-5-carboxylate as the starting material in place of ethyl (S)-2-pyrrolidone-5-carboxylate, the enantiomers of 15a and 15b are obtained as products.

Alternatively, compounds of Formula (I) where the pyrrolidine ring has (2S,4S) stereochemistry i.e, the groups at C-2 and C-4 position of the pyrrolidine ring are syn to each other can be prepared by heating compound 3 in dimethylfomamide in the presence of potassium cyanide as described in Esquerra, J., et al, *Tetrahedron*, 49, 8665 (1993). This reaction causes racemization at the C-4 carbon in 3 thus providing compounds of formula 3 wherein the —$CO_2Et$ and the -$alk^2$-$Ar^3$ groups are either syn or trans to each other. These diastereomers can be separated and then converted to a compound of Formula (I) as described above.

Compounds of Formula (I) where X is —CONH—, $R^1$ is methyl, $alk^1$ is —$(CH_2)_2$—, the other groups are as defined in the Summary of the Invention and the stereochemistry at the C2 and C4 carbons atoms in the pyrrolidine ring is (2S,4R) can be prepared as illustrated and described in Scheme IV below.

Scheme IV

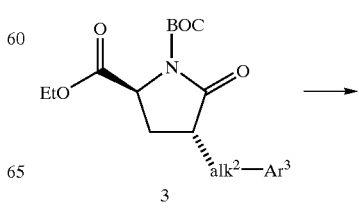

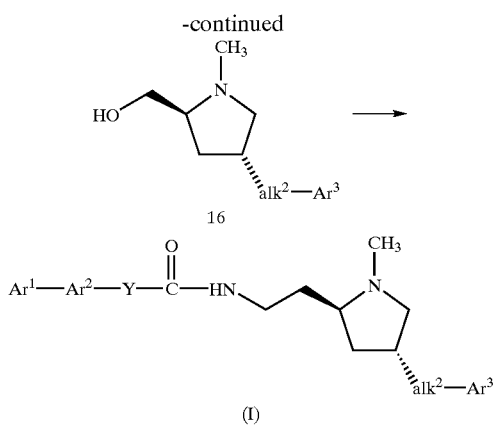

Prolonged heating of compound 3 with excess diborane in tetrahydrofuran, followed by heating with hydrochloric acid in methanol provides an N-methyl-2-hydroxymethylpyrrolidine derivative of formula 16. Compound 16 is then converted to a compound of Formula (I) where X is —CONH—, alk$^1$ is —(CH$_2$)$_2$—, the other groups are as defined in the Summary of the Invention and the stereochemistry at the pyrrolidine ring is (2S,4R) as described in Scheme II above.

Utility, Testing and Administration

General Utility

The compounds of the invention are CCR-3 receptor antagonists and inhibit eosinophil recruitment by CCR-3 chemokines such as RANTES, eotaxin, MCP-2, MCP-3 and MCP-4. Compounds of this invention and compositions containing them are useful in the treatment of eosiniphil-induced diseases such as inflammatory or allergic diseases and including respiratory allergic diseases such as asthma, allergic rhinitis, hypersensitivity lung diseases, hypersensitivity pneumonitis, eosinophilic pneumonias (e.g., chronic eosinophilic pneumonia); inflammatory bowel diseases (e.g., Crohn's disease and ulcerative colitis); and psoriasis and inflammatory dermatoses such as dermatitis and eczema.

Additionally, it has recently been discovered that the CCR-3 receptor plays a role in the pathogenesis of Acquired Immune Deficiency Syndrome (AIDS). Accordingly, the compounds of this invention and compositions containing them are also useful in the treatment of AIDS.

Testing

The CCR-3 antagonistic activity of the compounds of this invention was measured by in vitro assays such as ligand binding and chemotaxis assays as described in more detail in Examples 9, 10 and 11. In vivo activity was assayed in the Ovalbumin induced Asthma in Balb/c Mice Model as described in more detail in Example 12.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of Formula (I) may range from approximately 0.01–20 mg per kilogram body weight of the recipient per day; preferably about 0.1–10 mg/kg/day. Thus, for administration to a 70 kg person, the dosage range would most preferably be about 7 mg to 0.7 g per day.

In general, compounds of this invention will be administered as pharmaceutical compositions by any one of the following routes: oral, inhalation (e.g., intranasal or oral inhalation) or parenteral (e.g., intramuscular, intravenous or subcutaneous) administration. A preferred manner of administration is oral using a convenient daily dosage regimen which can be adjusted according to the degree of affliction. Compositions can take the form of tablets, pills, capsules, semisolids, powders, sustained release formulations, solutions, suspensions, liposomes, elixirs, or any other appropriate compositions. Another preferred manner for administering compounds of this invention is inhalation. This is an effective means for delivering a therapeutic agent directly to the respiratory tract for the treatment of diseases such as asthma and other similar or related respiratory tract disorders (see U.S. Pat. No. 5,607,915).

The choice of formulation depends on various factors such as the mode of drug administration and the bioavailability of the drug substance. For delivery via inhalation the compound can be formulated as liquid solutions or suspensions, aerosol propellants or dry powder and loaded into a suitable dispenser for administration. There are three types of pharmaceutical inhalation devices—nebulizer inhalers, metered-dose inhalers (MDI) and dry powder inhalers (DPI). Nebulizer devices produce a stream of high velocity air that causes the therapeutic agents (which has been formulated in a liquid form) to spray as a mist which is carried into the patient's respiratory tract. MDI's typically have the formulation packaged with a compressed gas. Upon actuation, the device discharges a measured amount of therapeutic agent by compressed gas, thus affording a reliable method of administering a set amount of agent. DPI's administer therapeutic agents in the form of a free flowing powder that can be dispersed in the patient's inspiratory air-stream during breathing by the device. In order to achieve a free flowing powder, the therapeutic agent is formulated with an excipient, such as lactose. A measured amount of the therapeutic is stored in a capsule form and is dispensed to the patient with each actuation. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I) in combination with at least one pharmaceutically acceptable excipient. Acceptable excipients are non-toxic, aid administration, and do not adversely affect the therapeutic benefit of the compound of Formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

For liposomal formulations of the drug for parenteral or oral delivery the drug and the lipids are dissolved in a suitable organic solvent e.g. tert-butanol, cyclohexane (1% ethanol). The solution is lypholized and the lipid mixture is suspended in an aqueous buffer an allowed to form a liposome. If necessary, the liposome size can be reduced by sonification. (see., Frank Szoka, Jr. and Demetrios Papahadjopoulos, "Comparative Properties and Methods of Preparation of Lipid Vesicles (Liposomes)", *Ann. Rev. Biophys. Bioeng.*, 9:467–508 (1980), and D. D. Lasic, "Novel Applications of Liposomes", *Trends in Biotech.*, 16:467–608, (1998))

Other suitable pharmaceutical excipients and their formulations are described in *Remington's Pharmaceutical Sciences,* edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01–99.99 wt % of a compound of Formula (I) based on the total formulation, with the balance being one or more suitable pharmaceutical excipients. Preferably, the compound is present at a level of about 1–80 wt %. Representative pharmaceutical formulations containing a compound of Formula (I) are described in Example 8.

EXAMPLES

The following preparations and examples are given to enable those skilled in the art to more clearly understand and to practice the present invention. They should not be considered as limiting the scope of the invention, but merely as being illustrative and representative thereof.

Synthetic Examples

Example 1

Synthesis of N-(2S,4R)-[4-(3,4-dichlorobenzyl)-1-tert-butoxycarbonylpyrrolidin-2-ylethyl]-2-[5-(3,4-dimethoxyphenyl)pyrimidin-2-ylsulfanyl]acetamide

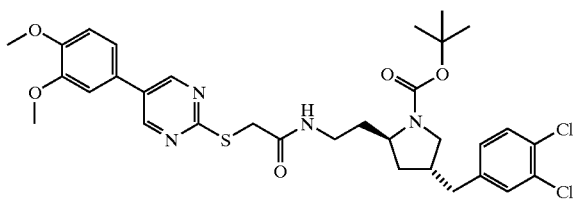

Step 1

To a solution of ethyl (S)-2-pyrrolidone-5-carboxylate (25.5 g, 162 mmol) in methylene chloride (250 mL) was added in order BOC anhydride (36.5 g, 167 mmol), triethylamine (24.8 mL, 178.4 mmol) and DMAP (2.0 g, 16.2 mmol), and the mixture was stirred at 20° C. for 16 hrs. Solvent was removed by evaporation under reduced pressure, and the resulting slurry was re-dissolved in EtOAc, washed with water and then dried over $Na_2SO_4$. Evaporation to dryness and then purification by a filtration chromatography on silica gel eluting with 50% EtOAc-hexane gave ethyl (S)-1-tert-butoxycarbonyl-2-pyrrolidone-5-carboxylate (38.3 g, 149.2 mmol) as an oil which crystallized on standing.

Step 2

A solution of ethyl (S)-1tert-butoxycarbonyl-2-pyrrolidone-5-carboxylate (5.0 g, 19.4 mmol) in dry THF (100 mL) was cooled to −78° C. while stirring under $N_2$, after which a 1.0M solution of lithium hexamethyldisilazide in THF (21.4 mL, 21.4 mmol) was added by syringe over 3 min. After stirring 12 min., HMPA (3.7 mL, 21.4 mmol) was added to the mixture by syringe, and after another 5 min. a solution of 3,4-dichlorobenzyl bromide (5.1 g, 21.4 mmol) in THF (10 mL) was added by addition funnel over 3 min. Stirring at −78° C. was continued for 1 hr, after which saturated aqueous $NH_4Cl$ (10 mL) was added and the mixture allowed to warm to room temperature. Standard work-up between EtOAc and $H_2O$ gave an oil which solidified. Purification was accomplished by two consecutive recrystallizations from acetone-hexane, which gave ethyl (2S,4R)-3-(3,4-dichlorobenzyl)-1-tert-butoxycarbonyl-2-pyrrolidone-5-carboxylate (5.68 g, 13.6 mmol) as a white crystalline product.

Step 3

To a solution of ethyl (2S,4R)-3-(3,4-dichlorobenzyl)-1-tert-butoxycarbonyl-2-pyrrolidone-5-carboxylate (1.92 g, 4.61 mmol) in freshly distilled THF (10 mL) was added a 1.0M solution of $BH_3$ in THF (46 mL, 46 mmol) and the mixture was warmed at 40° C. for 3.5 hrs. The mixture was then cooled in ice, excess $BH_3$ was destroyed by careful addition of methanol, and concentration by evaporation in vacuo gave a clear oil (3.02 g). Purification by chromatography on silica gel eluting with 40% EtOAc-hexane gave the pure (2S,4R)-4-(3,4-dichlorobenzyl)-1-tert-butoxycarbonyl-2-(hydroxymethyl)pyrrolidine (0.99 g, 2.75 mmol).

Step 4

To a solution of (2S,4R)-4-(3,4-dichlorobenzyl)-1-tert-butoxycarbonyl-2-(hydroxymethyl)pyrrolidine (1.38 g, 3.82 mmol) in methylene chloride (30 mL) was added triethylamine (0.78 mL, 5.72 mmol) followed by methanesulfonyl chloride (0.36 mL, 4.58 mmol) and the mixture was stirred at 20° for 9 hrs. Most $CH_2Cl_2$ was then removed by evaporation in vacuo, and the residue was diluted with ethyl acetate and washed with aqueous $NaHCO_3$ followed by water. Drying with $Na_2SO_4$ followed by evaporation in vacuo gave 1.70 g of crude (2S,4R)-4-(3,4-dichlorobenzyl)-1-tert-butoxycarbonyl-2-(methanesulfonyloxymethyl) pyrrolidine, which was used without further purification.

Step 5

Sodium cyanide (4.3 g, 87.4 mmol) was added to a solution of crude (2S,4R)-4-(3,4-dichlorobenzyl)-1-tert-butoxycarbonyl-2-(methanesulfonyloxymethyl)pyrrolidine (7.7 g, 17.5 mmol) in dry DMSO (120 mL) and the mixture was heated at 80° C. with stirring for 3.5 hrs. The reaction mixture was cooled and worked up between EtOAc and aqueous $Na_2CO_3$. Vacuum drying of the product afforded 6.34 g (17.2 mmol) of (2S,4R)-2-(cyanomethyl)-4-(3,4-dichloro-benzyl)-1-tert-butoxycarbonylpyrrolidine as an amber oil.

Step 6

To a solution of (2S,4R)-2-(cyanomethyl)-4-(3,4-dichloro-benzyl)-1-tert-butoxycarbonyl-pyrrolidine (6.34 g, 17.2 g) in dry THF (65 mL) was added a 1.0 M solution of BH$_3$ in THF (110 mL, 110 mmol) and the mixture was warmed at 45° C. for 1.5 hrs. The mixture was then cooled in ice and quenched by adding water dropwise until frothing ceased. The cold mixture was acidified with 2N HCl and then another 100 mL of 1N HCl was added, the mixture then being stored at 6° C. for 16 hrs. The clear solution was made basic with aqueous Na$_2$CO$_3$ and the resulting emulsion then extracted with CH$_2$Cl$_2$, completion of the workup then affording 7.3 g of crude product. Purification by chromatography on silica gel eluting with 0.5% conc. NH$_4$OH and 10–15% CH$_3$OH in CH$_2$Cl$_2$ gave pure (2S,4R)-2-(2-aminoethyl)-4-(3,4-dichloro-benzyl)-1-tert-butoxycarbonylpyrrolidine (4.40 g, 11.8 mm) as a clear oil.

Step 7

A slurry of chloromethylenedimethylammonium chloride (Vilsmeier salt; 25.0 g, 195.3 mmol; Aldrich) in DMF (45 mL) was stirred with ice-cooling for 15 min, after which 3,4-dimethoxyphenylacetic acid (12.8 g, 65.1 mmol) was added portionwise over 10 min. The reaction was stirred at 0° C. for another 10 min and then the temperature was raised to 65° C. After 20 min the temperature was raised to 85° C for 1 hr, and then the mixture was allowed to cool. The mixture was poured into ice water (200 mL) and sodium perchlorate (9.2 g, 65.1 mmol) and the mixture was stirred at 0° C. until the salt dissolved and crystallization of the product began. After standing at 0° C. for 16 hr the product was collected by filtration and washed with small amounts of ice water and cold ethanol, followed by ethyl ether. Vacuum drying afforded product 2-(3,4-dimethoxyphenyl)trimethinium perchlorate (17.4 g, 48.0 mmol) as an off-white solid.

Step 8

To a slurry of 2-(3,4-dimethoxyphenyl)trimethinium perchlorate (17.4 g, 47.9 mmol) in DMF (60 mL) and thiourea (5.11 g, 67.1 mmol) in absolute EtOH (160 mL) was added a solution of sodium ethoxide in ethanol (2.7M, 43 mL, 115 mmol) and the mixture was heated at 75° C. for 3 h. The mixture was cooled, neutralized with acetic acid, and poured into icewater. Filtration of the resulting fine precipitate, water washing and vacuum drying gave 5-(3,4-dimethoxyphenyl)-2-thiolpyrimidine (11.5 g, 46.3 mL) as a yellow solid.

Step 9

To a slurry of 5-(3,4-dimethoxyphenyl)-2-thiolpyrimidine (2.49 g, 10.0 mmol) in DMF (60 mL) was added a 60% suspension of sodium hydride in oil (0.42 g, 10.5 mmol). After stirring at 20° C. for 1 hr ethyl bromoacetate (1.8 g, 11.0 mmol) was added, and stirring was continued for 20 h. The mixture was poured into water and extracted with EtOAc to give the crude product. Purification by chromatography, eluting with 25% acetone-hexane, gave ethyl 5-(3,4-dimethoxy-phenyl)pyrimidin-2-yl]acetate as a yellow oil (2.83 g, 8.46 mmol).

Step 10

To a solution of ethyl 5-(3,4-dimethoxy-phenyl)pyrimidin-2-yl]acetate (2.83 g, 8.46 mmol) in EtOH (40 mL) was added a solution of LiOH.H$_2$O (0.53 g, 12.7 mmol) in water (8 mL). After stirring at 20° for 2 hr the resulting slurry was diluted with water and then acidified with 2N aqueous HCl. The resulting mixture was extracted with EtOAc to isolate the product. Crystallization from EtOAc-hexane then afforded 5-(3,4-dimethoxy-phenyl)pyrimidin-2-yl]acetic acid (2.23 g, 7.28 mmol) as fine yellow needles.

Step 11

To a solution of (2S,4R)-2-(2-aminoethyl)-4-(3,4-dichloro-benzyl)-1-tert-butoxycarbonyl-pyrrolidine (4.4 g, 11.8 mmol) in CH$_2$Cl$_2$ (120 mL) were added in order 5-(3,4-dimethoxyphenyl)-pyrimidin-2-ylthioacetic acid (4.3 g, 14.1 mmol) (prepared as described in Steps 7–10 above), EDCI (3.4 g, 17.7 mmol) and HOBT (0.4 g, 2.8 mmol). The reaction mixture was stirred at 20° C. for 2 hrs, after which workup between CH$_2$Cl$_2$ and aqueous NaHCO$_3$ followed by chromatographic purification on silica gel, eluting with 50% acetone-hexane, gave N-(2S,4R)-[4-(3,4-dichlorobenzyl)-1-tert-butoxycarbonylpyrrolidin-2-ylethyl]-2-[5-(3,4-dimethoxyphenyl)-pyrimidin-2-ylsulfanyl]acetamide (5.5 g, 8.3 mmol).

Example 2

Synthesis of N-(2S,4R)-[4-(3,4-dichlorobenzyl)pyrrolidin-2-ylethyl]-2-[5-(3,4-dimethoxyphenyl)pyrimidin-2-ylsulfanyl]acetamide hydrochloride

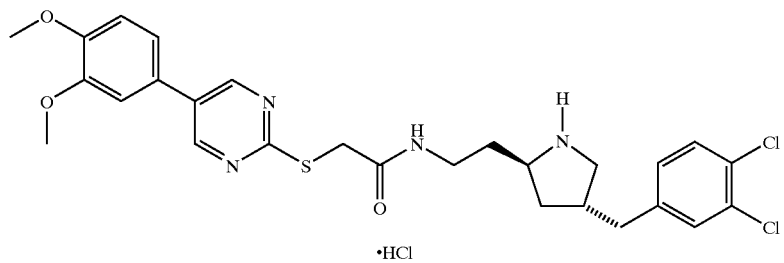

Step 1

N-(2S,4R)-[4-(3,4-Dichlorobenzyl)-1-tert-butoxycarbonylpyrrolidin-2-ylethyl]-2-[5-(3,4-dimethoxyphenyl)pyrimidin-2-ylsulfanyl]acetamide hydrochloride (5.5 g, 8.3 mmol) was deprotected by stirring it with triflouroacetic acid (0.25 mL) in CH$_2$Cl$_2$ solution (3 mL) for 16 hrs. Workup of the reaction mixture between CH$_2$Cl$_2$ and aqueous Na$_2$CO$_3$ gave the free amine as an oil. The product was purified by chromatography on silica gel eluting with 3% isopropylamine and 15% methanol in EtOAc, and the product was then converted to the HCl salt by treatment with one equivalent of HCl/Et$_2$O. The product was dried under vacuum affording N-(2S,4R)-[4-(3,4-dichlorobenzyl)pyrrolidin-2-ylethyl]-2-[5-(3,4-dimethoxyphenyl)pyrimidin-2-ylsulfanyl]-acetamide hydrochloride (4.33 g, 7.24 mmol) as a yellow solid, mp 100.5–102.1° C., mass spectrum 561(MH+).

Proceeding as described in Examples 1 and 2 above but substituting ethyl (S)-2-pyrrolidone-5-carboxylate with ethyl (R)-2-pyrrolidone-5-carboxylate provided N-(2R,4S)-[4-(3,4-dichlorobenzyl)pyrrolidin-2-ylethyl]-2-[5-(3,4-dimethoxyphenyl)pyrimidin-2-ylsulfanyl]-acetamide hydrochloride.

Proceeding as described in Examples 1 and 2 above but substituting 5-(3,4-dimethoxyphenyl)-pyrimidin-2-ylthioacetic acid with 5-(3,4-dimethoxyphenyl)pyrimidin-2-ylpropionic acid provided N-(2S,4R)-[4-(3,4-dichlorobenzyl)pyrrolidin-2-ylethyl]-3-[5-(3,4-dimethoxyphenyl)-pyrimidin-2-yl]propionamide hydrochloride.

Proceeding as described in Examples 1 and 2 above but substituting 5-(3,4-dimethoxy-phenyl)pyrimidin-2-ylthioacetic acid with 5-(phenyl)pyrimidin-2-ylthioacetic acid provided N-(2S,4R)-[4-(3,4-dichlorobenzyl)pyrrolidin-2-ylethyl]-2-[5-(phenyl)pyrimidin-2-ylsulfanyl]-acetamide hydrochloride.

Proceeding as described in Examples 1 and 2 above but substituting 5-(3,4-dimethoxy-phenyl)pyrimidin-2-ylthioacetic acid with 5-(phenyl)pyrimidin-2-ylthioacetic acid and substituting ethyl (S)-2-pyrrolidone-5-carboxylate with ethyl (R)-2-pyrrolidone-5-carboxylate provided N-(2R,4S)-[4-(3,4-dichlorobenzyl)pyrrolidin-2-ylethyl]-2-[5-(phenyl)pyrimidin-2-ylsulfanyl]acetamide hydrochloride.

Example 3

Synthesis of N-(2R,4R)-[4-(3,4-dichlorobenzyl)-1-methylpyrrolidin-2-ylmethyl]-2-[5-(phenyl)pyrimidin-2-ylsulfanyl]acetamide

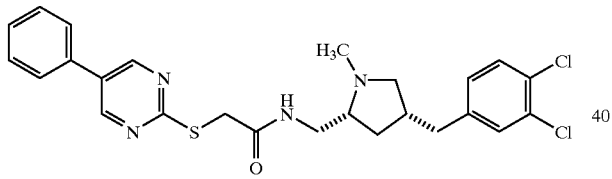

Step 1

To an ethanol solution of ethyl (2R,4S)-3-(3,4-dichlorobenzyl)-1-tert-butoxycarbonyl-2-pyrrolidone-5-carboxylate (prepared as described in Example 1, Steps 1 & 2 above, but substituting ethyl (S)-2-pyrrolidone-5-carboxylate with ethyl (R)-2-pyrrolidone-5-carboxylate) (1.0 g, 2.4 mmol) was added 1N HCl in ether (12 mL, 12 mmol). The reaction mixture was stirred for 6 h at 55° C. The reaction mixture was cooled to room temperature, diluted with ethyl acetate, and washed with aqueous NaHCO$_3$. The organic layer was dried over MgSO$_4$, filtered, and concentrated. Flash chromatography (50% hexanes/50% EtOAc) provided ethyl (2R,4S)-3-(3,4-dichlorobenzyl)-2-pyrrolidone-5-carboxylate (543 mg, 1.72 mmol).

Step 2

A THF solution of ethyl (2R,4S)-3-(3,4-dichlorobenzyl)-2-pyrrolidone-5-carboxylate (685 mg, 2.17 mmol) was added to a mixture of 60% NaH (130 mg, 3.25 mmol) stirring in THF at room temperature. After 1 h methyl iodide (0.27 mL, 4.34 mmol) was added. After 6 h the reaction mixture was quenched by addition of NH$_4$Cl solution. The reaction mixture was then diluted with EtOAc and washed with brine. The organic layer was dried over MgSO$_4$, filtered, and concentrated. Flash chromatography (60% hexanes/40% EtOAc) provided the less polar anti isomer ethyl (2R,4S)-3-(3,4-dichlorobenzyl)-1-methyl-2-pyrrolidone-5-carboxylate (216 g, 0.66 mmol) and more polar syn isomer ethyl (2R,4R)-3-(3,4-dichlorobenzyl)-1-methyl-2-pyrrolidone-5-carboxylate (130 mg, 0.4 mmol).

Step 3

To isomer ethyl (2R,4R)-3-(3,4-dichlorobenzyl)-1-methyl-2-pyrrolidone-5-carboxylate (910 mg, 2.76 mmol) was added 30 mL of 2.0M NH$_3$ in methanol. The reaction mixture was stirred for 120 h at room temperature. The reaction mixture was concentrated to provide a white solid. The solid was suspended in ether and filtered off to provide isomer (2R,4R)-5-aminocarbonyl-4-(3,4-dichlorobenzyl)-1-methylpyrrolidone (659 mg, 2.19 mmol) [MS: 301].

Step 4

To (2R,4R)-5-aminocarbonyl-4-(3,4-dichlorobenzyl)-1-methyl-2-pyrrolidone (620 mg, 2.06 mmol) was added 1.0 M BH$_3$/THF (14.4 mL, 14.4 mmol), and the mixture was heated at 70° C. for 3.5 h, stirred at 20° C. for 15 h, and then concentrated. Methanol was slowly added to the concentrated reaction mixture followed by 7 mL of 6N HCl. This mixture was then stirred for 1 h at 55° C., cooled to room temperature, diluted with water and basified with 1N aqueous NaOH, and the product extracted into EtOAc. Additional product was obtained by concentrating the aqueous layer and washing the resultant solids with EtOAc. The combined organic layers were dried over MgSO$_4$, filtered, and concentrated to provide (2R,4R)-2-aminomethyl-4-(3,4-dichlorobenzyl)-1-methylpyrrolidine (353 mg, 1.29 mmol).

Step 5

To a CH$_2$Cl$_2$ solution of (2R,4R)-2-aminomethyl-4-(3,4-dichlorobenzyl)-1-methyl-pyrrolidine (prepared as described in example 4.4) (40 mg, 0.15 mmol) was added 5-phenylpyrimidin-2-ylthioacetic acid (40 mg, 0.16 mmol), EDCI (36 mg, 0.19 mmol), and HOBT (2 mg, 0.015 mmol) The reaction mixture was stirred for 16 h at room temperature and then diluted with EtOAc and washed with aqueous NaHCO$_3$. The organic layer was dried over MgSO$_4$, filtered, and concentrated. Flash chromatography (95% CH$_2$Cl$_2$/5% MeOH) provided N-(2R,4R)-[4-(3,4-dichlorobenzyl)-1-methylpyrrolidin-2-ylmethyl]-2-[5-(phenyl)pyrimidin-2-ylsulfanyl]acetamide hydrochloride (47 mg, 0.098 mmol) mass spectrum 502 (MH+).

Proceeding as described in Example 3, step 1 above but substituting ethyl (2R,4S)-3-(3,4-dichlorobenzyl)-1-tert-butoxycarbonyl-2-pyrrolidone-5-carboxylate with ethyl (2S,4R)-3-(3,4-dichlorobenzyl)-1-tert-butoxycarbonyl-2-pyrrolidone-5-carboxylate, followed by methylation as described in Step 2, Example 3 above, provided ethyl (2S,4S)-3-(3,4-dichlorobenzyl)-1-methyl-2-pyrrolidone-5-carboxylate after chromatography. Ethyl (2S,4S)-3-(3,4-dichlorobenzyl)-1-methyl-2-pyrrolidone-5-carboxylate was then converted to N-(2S,4S)-[4-(3,4-dichlorobenzyl)-1-methylpyrrolidin-2-ylmethyl]-2-[5-(phenyl)pyrimidin-2-ylsulfanyl]acetamide by following Steps 3–5 as described in Example 3 above.

Example 4

Synthesis of N-(2R,4S)-[4-(3,4-dichlorobenzyl)-1-methylpyrrolidin-2-ylmethyl]-2-[5-(phenyl)pyrimidin-2-ylsulfanyl]acetamide

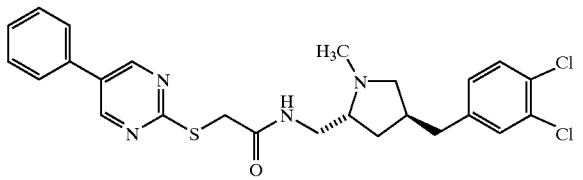

Step 1

A solution of ethyl (2R,4S)-3-(3,4-dichlorobenzyl)-1-methyl-2-pyrrolidone-5-carboxylate (prepared as described in Example 3 above) (216 mg, 0.65 mmol) in 2.0 M $NH_3$ in MeOH (10 mL, 20 mmol) was stirred at room temperature for 96 h. The reaction mixture was then concentrated to dryness to provide (2R, 4S)-5-aminocarbonyl-3-(3,4-dichlorobenzyl)-1-methyl-2-pyrrolidone (196 mg, 0.65 mmol).

Step 2

To (2R,4S)-5-aminocarbonyl-3-(3,4-dichlorobenzyl)-1-methyl-2-pyrrolidone (196 mg, 0.65 mmol) was added a solution of 1.0M BH3 in THF (5 mL, 5 mmol). The reaction mixture was stirred at 70° C. for 3.5 h after which it was concentrated in vacuo. Methanol was slowly added followed by 5 mL 6N HCl and the mixture was heated at 70° C. for 1 h. The reaction mixture was cooled to room temperature, basified with 1N NaOH, and the product extracted into EtOAc. The aqueous layer was concentrated to dryness and the resultant solids washed with EtOAc. The combined extracts were dried over $MgSO_4$, filtered, and concentrated. Flash chromatography (95% CH2Cl2/4% MeOH/1% $NH_4OH$) provided (2R,4S)-2-aminomethyl-3-(3,4-dichlorobenzyl)-1-methylpyrrolidine (1117 mg, 0.43 mmol).

Step 3

To a solution of (2R,4S)-2-aminomethyl-3-(3,4-dichlorobenzyl)-1-methylpyrrolidine (24 mg, 0.088 mmol) in $CH_2Cl_2$ (5 mL) was added 5-phenyl-pyrimidin-2-ylthioacetic acid (24 mg, 0.097 mmol), EDCI (21 mg, 0.11 mmol) and HOBT (1 mg, 0.009 mmol). The reaction mixture was stirred for 2 h at room temperature and then diluted with EtOAc and washed with $NaHCO_3$. The organic layer was dried over $MgSO_4$, filtered, and concentrated to provide N-(2R,4S)-[4-(3,4-dichlorobenzyl)-1-methylpyrrolidin-2-ylmethyl]-2-[5-(phenyl)pyrimidin-2-ylsulfanyl]-acetamide (30 mg, 0.06 mmol) mass spectrum 502 ($MH^+$).

Proceeding as described in Example 4, but substituting (2R,4S)-3-(3,4-dichlorobenzyl)-1-tert-butoxycarbonyl-2-pyrrolidone-5-carboxylate with (2S,4R)-3-(3,4-dichlorobenzyl)-1-tert-butoxycarbonyl-2-pyrrolidone-5-carboxylate (prepared as described in Example 3 above) provided N-(2S,4R)-[4-(3,4-dichlorobenzyl)-1-methylpyrrolidin-2-ylmethyl]-2-[5-(phenyl)pyrimidin-2-ylsulfanyl]-acetamide.

Example 5

Synthesis of N-(2S,4R)-[4-(3,4-dichlorobenzyl)-1-methylpyrrolidin-2-ylethyl]-2-[5-(phenyl)pyrimidin-2-ylsulfanyl]acetamide

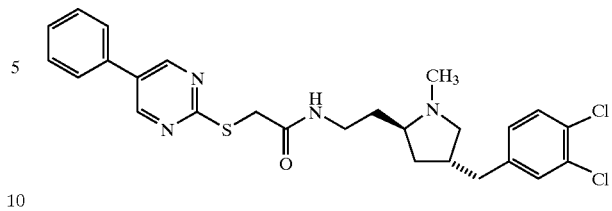

Step 1

To ethyl (2S,4R)-3-(3,4-dichlorobenzyl)-1-tert-butoxycarbonyi-2-pyrrolidone-5-carboxylate (prepared as described in Example 2 above) (1 g, 2.4 mmol) was added 1.0M $BH_3$/THF (36 mL, 36 mmol), and the reaction mixture was stirred at 70° C. for 50 h and then concentrated. MeOH was slowly added to the reaction mixture followed by 36 mL 1.0 M HCL in ether, followed by heating at 70° C. for 1 h. This mixture was then concentrated, diluted with EtOAc and then washed with aqueous $NaHCO_3$. The organic layer was dried over $MgSO_4$, filtered, and concentrated. Flash chromatography (95% $CH_2Cl_2$/4% MeOH/1% $NH_4OH$) provided (2S,4R)-2-hydroxymethyl-3-(3,4-dichlorobenzyl)-1-methylpyrrolidine (216 mg, 0.79 mmol).

Step 2

To a room temperature solution of (2S,4R)-2-hydroxymethyl-3-(3,4-dichlorobenzyl)-1-methylpyrrolidine (212 mg, 0.77 mmol) in $CH_2Cl_2$ (10 mL) was added triethylamine (0.161 mL, 1.16 mmol) followed by methanesulfonyl chloride (0.072 mL, 0.93 mmol). After 3.5 h the reaction mixture was diluted with EtOAc and washed 2× with aqueous $NaHCO_3$. The organic layer was dried over $MgSO_4$, filtered, and concentrated to provide (2S,4R)-3-(3,4-dichloro-benzyl)-2-(methanesulfonyloxymethyl-1-methylpyrrolidine (211 mg, 0.6 mmol).

Step 3

To a solution of (2S,4R)-3-(3,4-dichlorobenzyl)-2-(methanesulfonyloxymethyl-1-methylpyrrolidine (211 mg, 0.6 mmol) in DMSO was added sodium cyanide (176 mg, 3.6 mmol) and the mixture was heated at 70° C. for 21 h. The reaction mixture was diluted with EtOAc and washed 3× with aqueous $NaHCO_3$. The organic layer was dried over $MgSO_4$, filtered, and concentrated. Flash chromatography (60% EtOAc/40% hexanes) provided (2S,4R)-2-cyanomethyl-3-(3,4-dichlorobenzyl)-1-methylpyrrolidine (104 mg, 0.37 mmol).

Step 4

To a solution of (2S,4R)-2-cyanomethyl-3-(3,4-dichlorobenzyl)-1-methylpyrrolidine (793 mg, 2.8 mmol) in THF (50 mL) was added 1.0M $BH_3$/THF (19.6 mL, 19.6 mmol). The reaction mixture was heated at 70° C. for 4 h and then concentrated. MeOH was added slowly to the concentrate followed by 10 mL of 6N HCl and the mixture was then heated to 70° C. for 1 h. The reaction mixture was cooled to room temperature, basified with 1N NaOH, and extracted with EtOAc. The aqueous layer which contained the product was concentrated to dryness. The resultant solid was triturated with EtOAc and the solids removed by filtration. The EtOAc extract was concentrated to provide (2S,4R)-2-(2-aminoethyl)-3-(3,4-dichlorobenzyl)-1-methylpyrrolidine (425 mg, 1.5 mmol).

Step 5

To a solution of (2S,4R)-2-(2-aminoethyl)-3-(3,4-dichlorobenzyl)-1-methylpyrrolidine (50 mg, 0.17 mmol) in $CH_2Cl_2$ (5 mL) was added 5-phenylpyrimidin-2-ylthioacetic acid (47 mg, 0.19 mmol), EDCI (42 mg, 0.22 mmol), and HOBT (2.3 mg, 0.017 mmol). The reaction mixture was stirred for 72 h at room temperature, then diluted with EtOAc and washed 2X with aqueous $NaHCO_3$. The organic layer was dried over $MgSO_4$, filtered, and concentrated. Flash chromatography (95% CH2Cl2/4% MeOH/1% $NH_4OH$) provided N-(2S,4R)-[4-(3,4-dichlorobenzyl)-1-methylpyrrolidin-2-ylethyl]-2-[5-(phenyl)pyrimidin-2-ylsulfanyl]acetamide (60 mg, 0.12 mmol), mass spectrum 516 ($MH^+$).

Example 6

Synthesis of N-(2S,4R)-[4-(3,4-dichlorobenzyl)-1-(methoxycarbonylmethylcarbonyl)pyrrolidin-2-ylethyl]-2-[5-(3,4-dimethoxyphenyl)pyrimidin-2-ylsulfanyl]acetamide Proceeding as described in Example 6 above, but substituting monomethoxy malonyl chloride with acetyl chloride provides N-(2S,4R)-[4-(3,4-dichlorobenzyl)-1-(acetyl)pyrrolidin-2-ylethyl]-2-[5-(3,4-dimethoxyphenyl)pyrimidin-2-ylsulfanyl]acetamide.

Proceeding as described in Example 6 above, but substituting monomethoxy malonyl chloride with methanesulfonyl chloride provides N-(2S,4R)-[4-(3,4-dichlorobenzyl)-1-(methanesulfonyl)pyrrolidin-2-ylethyl]-2-[5-(3,4-dimethoxyphenyl)pyrimidin-2-ylsulfanyl]-acetamide

Example 7

Synthesis of N-(2S,4R)-[4-(3,4-dichlorobenzyl)-1-(carboxymethylcarbonyl)pyrrolidin-2-ylethyl]-2-[5-(3,4-dimethoxyphenyl)pyrimidin-2-ylsulfanyl]acetamide

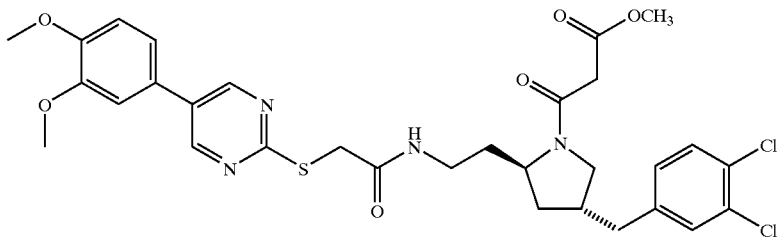

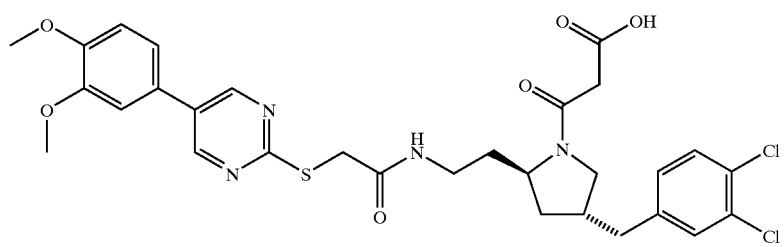

To an ice-cooled solution of N-(2S,4R)-[4-(3,4-dichlorobenzyl)pyrrolidin-2-ylethyl]-2-[5-(3,4-dimethoxyphenyl)pyrimidin-2-ylsulfanyl]acetamide (prepared as described in Example 1 above) (95 mg, 0.16 mmol) in $CH_2Cl_2$ (5 mL) was added triethylamine (1.0 mL), monomethoxy malonyl chloride (24 mg, 0.19 mmol) and a crystal of DMAP. The mixture was allowed to warm and stir at 20° C. for 1 hr and was then stored at 0° C. for 16 hr. Distribution of the mixture between EtOAc and water, water washing, drying and evaporation of the organic layer gave an orange residue which was purified by flash chromatography on silica gel. Elution with 60% acetone-hexane afforded 46 mg (0.07 mmol) of N-(2S,4R)-[4-(3,4-dichlorobenzyl)-1-(methoxycarbonyl-methylcarbonyl)pyrrolidin-2-ylethyl]-2-[5-(3,4-dimethoxyphenyl)pyrimidin-2-ylsulfanyl]-acetamide, mass spectrum 661 ($MH^+$).

To a solution of N-(2S,4R)-[4-(3,4-dichlorobenzyl)-1-(methoxycarbonyl-methylcarbonyl)pyrrolidin-2-ylethyl]-2-[5-(3,4-dimethoxyphenyl)pyrimidin-2-ylsulfanyl]-acetamide (prepared according to Example 6 above) (40 mg, 0.06 mmol) in $CH_3OH$ was added 0.3 mL of a freshly prepared 1N aqueous solution of LiOH. The solution was stirred under $N_2$ at 20° C. for 16 hrs, after which it was poured into water, the mixture then acidified with dilute aqueous $H_2SO_4$ and extracted with EtOAc. Drying and evaporation of the organic layer then afforded 33 mg of N-(2S,4R)-[4-(3,4-dichlorobenzyl)-1-(carboxymethylcarbonyl)pyrrolidin-2-ylethyl]-2-[5-(3,4-dimethoxyphenyl)pyrimidin-2-ylsulfanyl]acetamide (0.05 mmol) as a white amorphous foam, mass spectrum 647 ($MH^+$).

Example 8
Formulation Examples

The following are representative pharmaceutical formulations containing a compound of Formula (I).

Tablet Formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
|---|---|
| compound of this invention | 0.2 g |
| sodium acetate buffer solution, 0.4 M | 2.0 ml |
| HCl (1N) or NaOH (1N) | q.s. to suitable pH |
| water (distilled, sterile) | q.s. to 20 ml |

Liposomal Formulation

The following ingredients are mixed to form a liposomal formulation.

| Ingredient | Amount |
|---|---|
| compound of this invention | 10 mg |
| L-α-phosphatidylcholine | 150 mg |
| tert-butanol | 4 ml |

Freeze dry the sample and lyopholize overnight. Reconstitute the sample with 1 ml 0.9% saline solution. Liposome size can be reduced by sonication

Example 9

CCR-3 Receptor Binding Assay—in vitro

The CCR-3 antagonistic activity of the compounds of the invention was determined by their ability to inhibit the binding of $^{125}$I eotaxin to CCR-3 L1.2 transfectant cells ((see Ponath, P. D. et al., *J. Exp. Med.*, Vol. 183, 2437–2448, (1996)).

The assay was performed in Costar 96-well polypropylene round bottom plates. Test compounds were dissolved in DMSO and then diluted with binding buffer (50 mM HEPES, 1 mM $CaCl_2$, 5 mM $MgCl_2$, 0.5% bovine serum albumin (BSA), 0.02% sodium azide, pH 7.24) such that the final DMSO concentration was 2%. 25 μl of the test solution or only buffer with DMSO (control samples) was added to each well, followed by the addition of 25 μl of $^{125}$I-eotaxin (100 pmol) (NEX314, New England Nuclear, Boston, Mass.) and $1.5 \times 10^5$ of the CCR-3 L1.2 transfected cells in 25 μl binding buffer. The final reaction volume was 75 μl.

After incubating the reaction mixture for 1h at room temperature, the reaction was terminated by filtering the reaction mixture through polyethylenimine treated Packard Unifilter GF/C filter plate (Packard, Chicago, Ill.). The filters were washed four times with ice cold wash buffer containing 10 mm HEPES and 0.5M sodium chloride (pH 7.2) and dried at 65° C. for approximately 10 min. 25 μl/well of Microscint-20™ scintillation fluid (Packard) was added and the radioactivity retained on the filters was determined by using the Packard TopCount™.

Compounds of this invention were active in this assay.

The $IC_{50}$ value (concentration of test compound required to reduce $^{125}$I-eotaxin binding to the CCR-3 L 1.2 transfected cells by 50%) for compounds in Table I of the invention was between 0.02 and 200 μM.

Example 10

Inhibition of Eotaxin Mediated Chemotaxis of CCR-3 L1.2 Transfectant Cells—In vitro Assay The CCR-3 antagonistic activity of the compounds of this invention was determined by measuring the inhibition of eotaxin mediated chemotaxis of the CCR-3 L1.2 transfectant cells, using a slight modification of the method described in Ponath, P. D. et al., *J. Clin. Invest.* 97:604 –612 (1996). The assay was performed in a 24-well chemotaxis plate (Costar Corp., Cambridge Mass.). CCR-3 L1.2 transfectant cells were grown in culture medium containing RPMI 1640, 10% Hyclone™ fetal calf serum, 55 mM 2-mercaptoethanol and Geneticin 418 (0.8 mg/ml). 18–24 hours before the assay, the transfected cells were treated with n-butyric acid at a final concentration of 5 nM/$1 \times 10^6$ cells/ml, isolated and resuspended at $1 \times 10^7$ cells/ml in assay medium containing equal parts of RPMI 1640 and Medium 199 (M 199) with 0.5% bovine serum albumin.

Human eotaxin suspended in phosphate buffered saline at 1 mg/ml was added to bottom chamber in a final concentration of 100 nm. Transwell culture inserts (Costar Corp., Cambridge Mass.) having 3 micron pore size were inserted into each well and L1.2 cells ($1\times10^6$) were added to the top chamber in a final volume of 100 μl. Test compounds in DMSO were added both to the top and bottom chambers such that the final DMSO volume was 0.5%. The assay was performed against two sets of controls. The positive control contained cells with no test compound in the top chamber and only eotaxin in the lower chamber. The negative control contained cells with no test compound in the top chamber and neither eotaxin nor test compound in lower chamber. The plate was incubated at 37° C. After 4 h, the inserts were removed from the chambers and the cells that had migrated to the bottom chamber were counted by pipetting out 500 μl of the cell suspension from the lower chamber to 1.2 ml Cluster tubes (Costar) and counting them on a FACS for 30 sec.

The $IC_{50}$ value (concentration of test compound required to reduce eotaxin mediated chemotaxis of CCR-3 L 1.2 transfected cells by 50%) for representative compounds of the invention was between 0.006 to 1.1 μm.

Example 11

Inhibition of Eotaxin mediated chemotaxis of human eosinophils—In vitro Assay

The ability of compounds of the invention to inhibit eotaxin mediated chemotaxis of human eosinophils was assessed using a slight modification of procedure described in Carr, M. W. et al., Proc. Natl. Acad. Sci. U.S.A., 91: 3652–3656 (1994). Experiments were performed using 24 well chemotaxis plates (Costar Corp., Cambridge Mass.). Eosinophils were isolated from blood using the procedure described in PCT Application, Publication No. WO 96/22371. The endothelial cells used were the endothelial cell line ECV 304 obtained from European Collection of Animal Cell Cultures (Porton Down, Salisbury, U.K.). Endothelial cells were cultured on 6.5 mm diameter Biocoat® Transwell tissue culture inserts (Costar Corp., Cambridge Mass.) with a 3.0 μM pore size. Culture media for ECV 304 cells consisted of M199, 10% Fetal Calf Serum, L-glutamine and antibiotics. Assay media consisted of equal parts RPMI 1640 and M199, with 0.5% BSA. 24 h before the assay $2\times10^5$ ECV 304 cells were plated on each insert of the 24-well chemotaxis plate and incubated at 37° C. 20 nM of eotaxin diluted in assay medium was added to the bottom chamber. The final volume in bottom chamber was 600 μl. The endothelial coated tissue culture inserts were inserted into each well. $10^6$ eosinophil cells suspended in 100 μl assay buffer were added to the top chamber. Test compounds dissolved in DMSO were added to both top and bottom chambers such that the final DMSO volume in each well was 0.5%. The assay was performed against two sets of controls. The positive control contained cells in the top chamber and eotaxin in the lower chamber. The negative control contained cells in the top chamber and only assay buffer in the lower chamber. The plates were incubated at 37° C. in 5% $CO_2$/95% air for 1–1.5 h.

The cells that had migrated to the bottom chamber were counted using flow cytometry. 500 μl of the cell suspension from the lower chamber was placed in a tube, and relative cell counts were obtained by acquiring events for a set time period of 30 seconds.

Compounds of this invention were active in this assay.

Example 12

Inhibition of Eosinophil Influx into the Lungs of Ovalbumin Sensitized Balb/c Mice by CCR-3 Antagonist—In vivo Assay The ability of the compounds of the invention to inhibit leukocyte infiltration into the lungs was determined by measuring the inhibition of eosinophil accumulation into the bronchioalveolar lavage (BAL) fluid of Ovalbumin (OA)-sensitized balb/c mice after antigen challenge by aerosol. Briefly, male balb/c mice weighing 20–25 g were sensitized with OA (10 μg in 0.2 ml aluminum hydroxide solution) intraperitoneally on days 1 and 14. After a week, the mice were divided into ten groups. Test compound or only vehicle (control group) or anti-eotaxin antibody (positive control group) was administered either intraperitoneally, subcutaneously or orally. After 1 h, the mice were placed in a Plexiglass box and exposed to OA aerosol generated by a PARISTAR™ nebulizer (PARI, Richmond, Va.) for 20 min. Mice which had not been sensitized or challenged were included as negative control. After 24 or 72 h, the mice were anesthetized (urethane, approx. 1 g/kg, i.p.), a tracheal cannula (PE 60 tubing) was inserted and the lungs were lavaged four times with 0.3 ml PBS. The BAL fluid was transferred into plastic tubes and kept on ice. Total leukocytes in a 20 μl aliquot of the BAL fluid was determined by Coulter Counter™ (Coulter, Miami, Fla.). Differential leukocyte counts were made on Cytospin™ preparations which had been stained with a modified Wright's stain (Diff-Quick™) by light microscopy using standard morphological criteria.

Compounds of this invention were active in this assay. The ID50 for the compounds of this invention in this assay is between 30 and 50 mgs/kg.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed:

1. A compound of Formula (I):

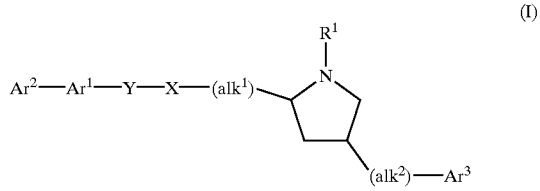

wherein:

$R^1$ is hydrogen, alkyl, acyl, heteroalkyl, —$CONR^3R^4$ (where $R^3$ and $R^4$ are independently hydrogen or alkyl), —$COOR^5$ (where $R^5$ is hydrogen, alkyl or heteroalkyl), or —$SO_2R^6$ where $R^6$ is alkyl;

$alk^1$ is an alkylene chain of 1 to 6 carbon atoms;

X is —NHCO— or —CONH—;

Y is an alkylene chain of 1 to 3 carbon atoms or an alkylene chain of 2 or 3 carbon atoms wherein one of the carbon atoms is replaced by a heteroatom selected from the group consisting of —O—, —NR$^b$— {where R$^b$ is hydrogen, alkyl, acyl, —CONR$^7$R$^8$ (where R$^7$ and R$^8$ are independently hydrogen or alkyl), —COOR$^9$ (where R$^9$ is hydrogen, alkyl or heteroalkyl), aryl, or aralkyl)} and —S(O)n— wherein n is 0 to 2;

Ar$^1$ is a heteroaryl group or phenyl group wherein the heteroaryl or phenyl group is substituted, in addition to the Ar$^2$ group, with a group selected from the group consisting of hydrogen, halo, alkyl, alkoxy, nitro, amido, aminosulfonyl and sulfonylamino;

Ar$^2$ is aryl;

alk$^2$ is an alkylene group of 1 to 6 carbon atoms wherein one of the carbon atoms is optionally replaced by —CO—, —NR$^c$— {where R$^c$ is hydrogen, alkyl, acyl, —CONR$^{10}$R$^{11}$ (where R$^{10}$ and R$^{11}$ are independently hydrogen or alkyl), —COOR$^{12}$ (where R$^{12}$ is hydrogen, alkyl or heteroalkyl), aryl, or aralkyl)} or —S(O)n1— wherein n1 is 0 to 2; and Ar$^3$ is cycloalkyl, aryl or heteroaryl; or a pharmaceutically acceptable salt thereof.

2. A compound of Formula (Ia):

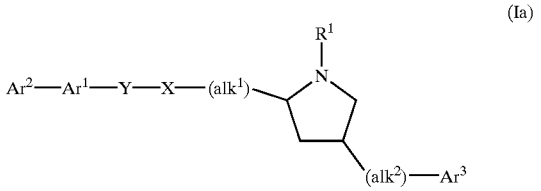

(Ia)

wherein

R$^1$ is hydrogen, alkyl, acyl, heteroalkyl, —CONR$^3$R$^4$ (where R$^3$ and R$^4$ are independently hydrogen or alkyl), —COOR$^5$ (where R$^5$ is hydrogen, alkyl or heteroalkyl), or —SO$_2$R$^6$ where R$^6$ is alkyl;

alk$^1$ is an alkylene chain of 1 to 6 carbon atoms;

X is —NHCO— or —CONH—;

Y is —O—(CH$_2$)—, —O—(CH$_2$)$_2$—, —O—(CHCH$_3$)—, —NR$^b$—(CH$_2$)—, —NR$^b$—(CH$_2$)$_2$—, —NR$^b$—(CHCH$_3$)— {where R$^b$ is hydrogen, alkyl, acyl, —CONR$^7$R$^8$ (where R$^7$ and R$^8$ are independently hydrogen or alkyl), —COOR$^9$ (where R$^9$ is hydrogen, alkyl or heteroalkyl), aryl, or aralkyl)], —S(O)n—(CH$_2$)—, —S(O)n—(CH$_2$)$_2$—, or —S(O)n—(CHCH$_3$)— where n is 0 to 2;

Ar$^1$ is a heteroaryl group or phenyl group wherein the heteroaryl or phenyl group is substituted, in addition to the Ar$^2$ group, with a substituent selected from the group consisting of hydrogen, halo, alkyl, alkoxy, nitro, amido, aminosulfonyl and sulfonylamino;

Ar$^2$ is aryl;

alk$^2$ is an alkylene chain of 1 to 6 carbon atoms wherein one of the carbon atoms is optionally replaced by —CO—, —NR$^c$— {where R$^c$ is hydrogen, alkyl, acyl, —CONR$^{10}$R$^{11}$ (where R$^{10}$ and R$^{11}$ are independently hydrogen or alkyl), —COOR$^{12}$ (where R$^{12}$ is hydrogen, alkyl or heteroalkyl), aryl, or aralkyl)} or —S(O)n1— wherein n1 is 0 to 2; and Ar$^3$ is cycloalkyl, aryl or heteroaryl; or a pharmaceutically acceptable salt thereof.

3. The compound of claim 2 wherein R$^1$ is hydrogen, alkyl, acyl, or —SO$_2$R$^a$ where R$^a$ is alkyl.

4. The compound of claim 3 wherein R$^1$ is hydrogen, methyl, acetyl, —COCH$_2$CO$_2$H, —COCH$_2$CO$_2$CH$_3$, or —CO$_2$-tert-butyl.

5. The compound of claim 2 wherein Y is —SCH$_2$—, —OCH$_2$— or —NHCH$_2$—.

6. The compound of claim 5 wherein X is —CONH—.

7. The compound of claim 6 wherein Y is —SCH$_2$—.

8. The compound of claim 6 wherein Y is —OCH$_2$—.

9. The compound of claim 8 wherein alk$^1$ and alk$^2$ are independently an alkylene chain of 1 or 2 carbon atoms.

10. The compound of claim 2 wherein Ar$^1$ is a heteroaryl group.

11. The compound of claim 3 wherein Ar$^1$ is pyrimidin-2-yl.

12. The compound of claim 11 wherein Y is —SCH$_2$— or —OCH$_2$—.

13. The compound of claim 12 wherein Ar$^2$ is aryl optionally substituted with one or two substituents selected from the group consisting of alkoxy, hydroxy, and halo.

14. The compound of claim 13 wherein Ar$^2$ is phenyl or 3,4-dimethoxyphenyl and is at the 5-position of the pyrimidin-2-yl.

15. The compound of claim 12 wherein alk$^2$ is —CH$_2$— and Ar$^3$ is aryl.

16. The compound of claim 15 wherein Ar$^3$ is 3,4-dichlorophenyl.

17. A compound of Formula (Ib):

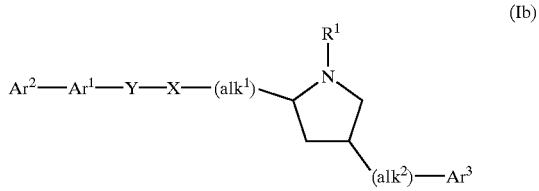

(Ib)

wherein:

R$^1$ is hydrogen, alkyl, acyl, heteroalkyl, —CONR$^3$R$^4$ (where R$^3$ and R$^4$ are independently hydrogen or alkyl), —COOR$^5$ (where R$^5$ is hydrogen, alkyl or heteroalkyl), or —SO$_2$R where R is alkyl;

alk$^1$ is an alkylene chain of 1 to 6 carbon atoms;

X is —NHCO— or —CONH—;

Y is:

(i) —(CH$_2$)—, —(CH$_2$)$_2$—, —(CH$_2$)$_3$—, —(CHCH$_3$)—, —(CHCH$_3$)—(CH$_2$)—, or —(CH$_2$)—(CHCH$_3$)—; or (ii) —(CH$_2$)—O—, —(CH$_2$)$_2$—O—, —(CHCH$_3$)—O—, —(CH$_2$)—NR$^b$—, —(CH$_2$)$_2$—NR$^b$—, or —(CHCH$_3$)—NR$^b$— {where R$^b$ is hydrogen, alkyl, acyl, —CONR$^7$R$^8$ (where R$^7$ and R$^8$ are independently hydrogen or alkyl), —COOR$^9$ (where R$^9$ is hydrogen, alkyl or heteroalkyl), aryl, or aralkyl)} when X is —CONH—;

Ar$^1$ is a heteroaryl group or phenyl group wherein the heteroaryl or phenyl group is substituted, in addition to the Ar$^2$ group, with a substituent selected from the group consisting of hydrogen, halo, alkyl, alkoxy, nitro, amido, aminosulfonyl and sulfonylamino;

Ar$^2$ is aryl;

alk$^2$ is an alkylene chain of 1 to 6 carbon atoms wherein one of the carbon atoms is optionally replaced by —CO—, —NR$^c$— {where R$^c$ is hydrogen, alkyl, acyl, —CONR$^{10}$R$^{11}$ (where R$^{10}$ and R$^{11}$ are independently hydrogen or alkyl), —COOR$^{12}$ (where R$^{12}$ is hydrogen, alkyl or heteroalkyl), aryl, or aralkyl)} or —S(O)n1— wherein n1 is 0 to 2; and Ar$^3$ is cycloalkyl, aryl or heteroaryl; or a pharmaceutically acceptable salt thereof.

18. The compound of claim 17 wherein $Ar^1$ is a heteroaryl group and $Ar^2$ is aryl optionally substituted with one or two substituents selected from the group consisting of alkoxy, hydroxy, and halo.

19. The compound of claim 18 wherein $Ar^1$ is pyrimidin-2-yl and $Ar^2$ is phenyl or 3,4-dimethoxyphenyl and is at the 5-position of the pyrimidin-2-yl.

20. A compound of Formula (Ib):

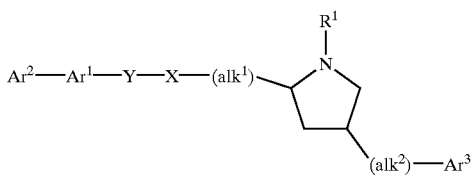

(Ib)

wherein:
$R^1$ is —COCH$_2$CO$_2$H, —COCH$_2$CO$_2$CH$_3$, or —CO$_2$-tert-butyl;
alk$^1$ is an alkylene chain of 1 to 6 carbon atoms;
X is —CONH—;
Y is:
  (i) —(CH$_2$)—, —(CH$_2$)$_2$—, —(CH$_2$)$_3$—, —(CHCH$_3$)—, —(CHCH$_3$)—(CH$_2$)—, or —(CH$_2$)—(CHCH$_3$)—; or
  (ii) —(CH$_2$)—O—, —(CH$_2$)$_2$—O—, —(CHCH$_3$)—O—, —(CH$_2$)—NR$^b$—, —(CH$_2$)$_2$—NR$^b$—, or —(CHCH$_3$)—NR$^b$— {where R$^b$ is hydrogen, alkyl, acyl, —CONR$^7$R$^8$ (where R$^7$ and R$^8$ are independently hydrogen or alkyl), —COOR$^9$ (where R$^9$ is hydrogen, alkyl or heteroalkyl), aryl, or aralkyl)} when X is —CONH—;
$Ar^1$ is pyrimidin-2-yl;
$Ar^2$ is phenyl or 3,4-dimethoxyphenyl and is at the 5-position of the pyrimidin-2-yl of $Ar^1$;
alk$^2$ is an alkylene chain of 1 to 6 carbon atoms wherein one of the carbon atoms is optionally replaced by —CO—, —NR$^c$— {where R$^c$ is hydrogen, alkyl, acyl, —CONR$^{10}$R$^{11}$ (where R$^{10}$ and R$^{11}$ are independently hydrogen or alkyl), —COOR$^{12}$ (where R$^{12}$ is hydrogen, alkyl or heteroalkyl), aryl, or aralkyl)) or —S(O)$_{n1}$— wherein n1 is 0 to 2; and
$Ar^3$ is cycloalkyl, aryl or heteroaryl; or
a pharmaceutically acceptable salt thereof.

21. A compound of the Formula (Ib):

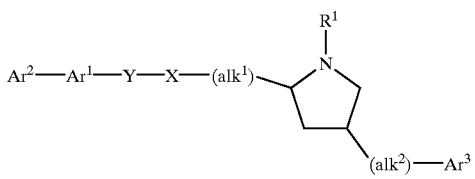

(Ib)

wherein:
$R^1$ is —COCH$_2$CO$_2$H, —COCH$_2$CO$_2$CH$_3$, or —CO$_2$-tert-butyl;
X is —CONH—;
Y and alk$^1$ are independently methylene or ethylene;
$Ar^1$ is pyrimidin-2-yl;
$Ar^2$ is phenyl or 3,4-dimethoxyphenyl and is at the 5-position of the pyrimidin-2-yl of $Ar^1$;

alk$^2$ is methylene; and
$Ar^3$ is 3,4-dichlorophenyl; or
a pharmaceutically acceptable salt thereof.

22. A pharmaceutical composition comprising a therapeutically effective amount of a compound of any one of claims 1 to 21 and a pharmaceutically acceptable excipient.

23. A method of treatment of a disease in a mammal treatable by administration of a CCR-3 receptor antagonist, comprising administration of a pharmaceutical composition comprising a therapeutically effective amount of a compound of any one of claims 1–21 and a pharmaceutically acceptable excipient.

24. The method of claim 23 wherein the disease is asthma.

25. A process for preparing a compound as claimed in claim 1, which process comprises:
coupling a compound having a formula 7,

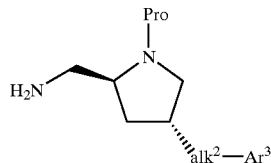

7 wherein Pro is a protective group, and alk$^2$ and $Ar^3$ are as defined in claim 1;
with a compound of formula 8:

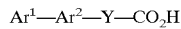

Ar$^1$—Ar$^2$—Y—CO$_2$H          8 wherein $Ar^1$, $Ar^2$ and Y are as described in claim 1;
removal of the protecting group to provide a compound of Formula (I)

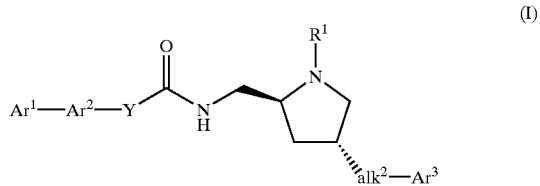

(I)

wherein $R^1$ is hydrogen, and $Ar^1$, $Ar^2$, alk$^2$ and $Ar^3$ are as defined in claim 1; and
conversion to compounds of Formula (I) wherein $R^1$ is acyl or sulfonyl with an acid halide of general formula $R^1$C(O)Hal or a sulfonyl halide of general formula $R^1$SO$_2$Hal, wherein Hal is a halo group.

26. A process for preparing a compound as claimed in claim 1, which process comprises
reduction of the cyano group of a compound having formula 10:

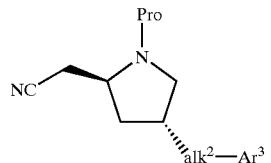

10 wherein Pro is a protective group, and alk$^2$ and $Ar^3$ are as defined in claim 1;

coupling with a compound of Formula 8:

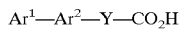     8 wherein $Ar^1$, $Ar^2$ and Y are as described in claim 1;
removal of the protecting group to provide a compound of Formula (I):

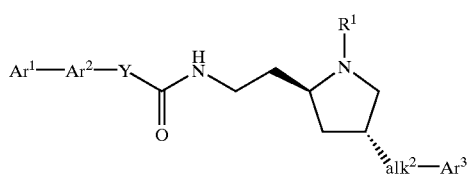     (I)

wherein $R^1$ is hydrogen, and $Ar^1$, $Ar^2$, $alk^2$ and $Ar^3$ are as defined in claim 1, and conversion to compounds of Formula (I) wherein $R^1$ is an acyl or sulfonyl group with an acid halide $R^1C(O)Hal$ or a sulfonyl halide $R^1SO_2Hal$, wherein Hal is a halo group.

27. A process for preparing a compound as claimed in claim 1, which process comprises coupling a compound having a formula 15a or 15b

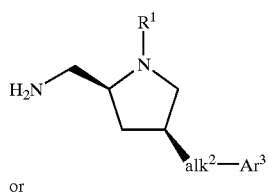     15a or

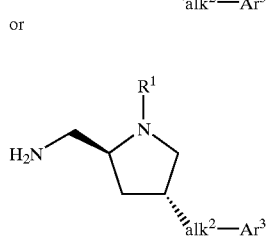     15b wherein $R^1$ is alkyl, and $alk^2$ and $Ar^3$ are as defined in claim 1,
with a compound of formula 8

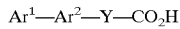     8 wherein $Ar^1$, $Ar^2$ and Y are as described in claim 1 to provide a compound of Formula (Ia) or (Ib)

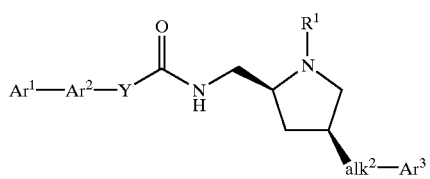     (Ia)

or

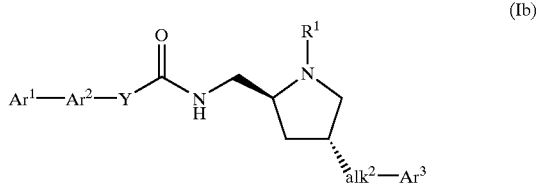     (Ib)

wherein $R^1$ is alkyl, $Ar^1$, $Ar^2$, $alk^2$ and $Ar^3$ are as defined in claim 1.

28. A process for preparing a compound as claimed in claim 1, which process comprises:

mesylating a compound having a formula 16,

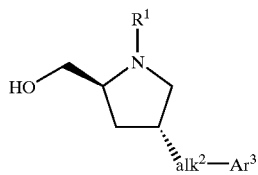     16 wherein $R^1$ is alkyl, and $alk^2$ and $Ar^3$ are as defined in claim 1;

converting to a cyanide followed by reduction, and coupling with a compound of formula 8

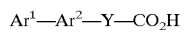

wherein $Ar^1$, $Ar^2$ and Y are as described in claim 1, to provide a compound of Formula (I)

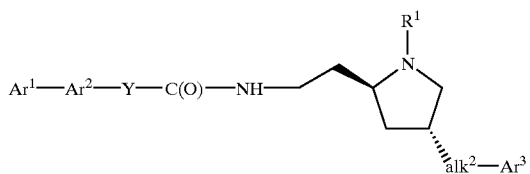     (I)

wherein $R^1$ is alkyl, and $Ar^1$, $Ar^2$, $alk^2$, $Ar^3$, and Y are as described in claim 1.

* * * * *